(12) United States Patent
Drayna et al.

(10) Patent No.: US 8,530,167 B2
(45) Date of Patent: Sep. 10, 2013

(54) DIAGNOSTIC AND THERAPEUTIC USES OF GNPTAB, GNPTG, AND NAGPA IN STUTTERING

(75) Inventors: Dennis T. Drayna, Potomac, MD (US); Changsoo Paul Kang, Gaithersburg, MD (US); Sheikh Riazuddin, Lahore (PK)

(73) Assignees: The United States of America, as represented by the Secretary, Department of Health and Human Services, Washington, DC (US); Centre of Excellence in Molecular Biology Together With All Allied Components, University of Punjab, Lahore (PK)

( * ) Notice: Subject to any disclaimer, the term of this patent is extended or adjusted under 35 U.S.C. 154(b) by 70 days.

(21) Appl. No.: 13/148,340

(22) PCT Filed: Feb. 8, 2010

(86) PCT No.: PCT/US2010/023437
§ 371 (c)(1),
(2), (4) Date: Aug. 31, 2011

(87) PCT Pub. No.: WO2010/091328
PCT Pub. Date: Aug. 12, 2010

(65) Prior Publication Data
US 2011/0313029 A1    Dec. 22, 2011

Related U.S. Application Data

(60) Provisional application No. 61/150,954, filed on Feb. 9, 2009.

(51) Int. Cl.
*C12Q 1/68* (2006.01)
*C07H 21/04* (2006.01)

(52) U.S. Cl.
USPC .......................... 435/6.13; 435/6.1; 536/23.2

(58) Field of Classification Search
None
See application file for complete search history.

(56) References Cited

PUBLICATIONS

Fisher et al., "Genetic susceptibility to stuttering," *N. Engl. J. Med.*, 362 (8), 750-752 (2010).
Hussain et al., "The prevalence and demographic characteristics of consanguineous marriages in Pakistan," *J. Biosoc. Sci.*, 30 (2), 261-275 (1998).
International Search Report, Application No. PCT/US2010/023437, dated Jul. 5, 2010.
Jaber et al., "The impact of consanguinity worldwide," *Community Genet.*, 1 (1), 12-17 (1998).
Kang et al., "Mutations in the Lysosomal Enzyme—Targeting Pathway and Persistent Stuttering," *N. Engl. J. Med.*, 362 (8), 677-685 (2010).
Kudo et al., "Mucolipidosis II (I-Cell Disease) and Mucolipidosis IIIA (Classical Pseudo-Hurler Polydystrophy) Are Caused by Mutations in the GlcNAc-Phosphotransferase $\alpha/\beta$—Subunits Precursor Gene," *Am. J. Hum. Genet.*, 78, 451-463 (2006).
Riaz et al., "Genomewide Significant Linkage to Stuttering on Chromosome 12," *Am. J. Hum. Genet.*, 76 (4), 647-651 (2005).
Sly et al., "Brain-directed gene therapy for lysosomal storage disease: Going well beyond the blood—brain barrier," *Proc. Natl. Acad. Sci. U.S.A.*, 99 (9), 5760-5762 (2002).
Suresh et al., "New Complexities in the Genetics of Stuttering: Significant Sex-Specific Linkage Signals," *Am. J. Hum. Genet.*, 78 (4), 554-563 (2006).
Tiede et al., "Mucolipidosis II is caused by mutations in *GNPTA* encoding the $\alpha/\beta$ GlcNAc-1-phosphotransferase," *Nat. Med.*, 11 (10), 1109-1112 (2005).
Werber, "Lysosomal storage diseases market," *Nat. Rev. Drug Discov.*, 3 (1), 9-10 (2004).
Wittke-Thompson et al., "Genetic studies of stuttering in a founder population," *J. Fluency Disord.*, 32 (1), 33-50 (2007).

*Primary Examiner* — Tekchand Saidha
*Assistant Examiner* — Md. Younus Meah
(74) *Attorney, Agent, or Firm* — Leydig, Voit & Mayer

(57) ABSTRACT

The allelic variants or mutations in three genes: GNPTAB, GNPTG and NAGPA, that correlate with stuttering in humans, as well as the encoded mutated polypeptides and related vectors, host cells, antibodies, antibody-producing cell lines and methods of diagnosing, prognosticating and treating stuttering are provided.

2 Claims, 16 Drawing Sheets

Figure 2:
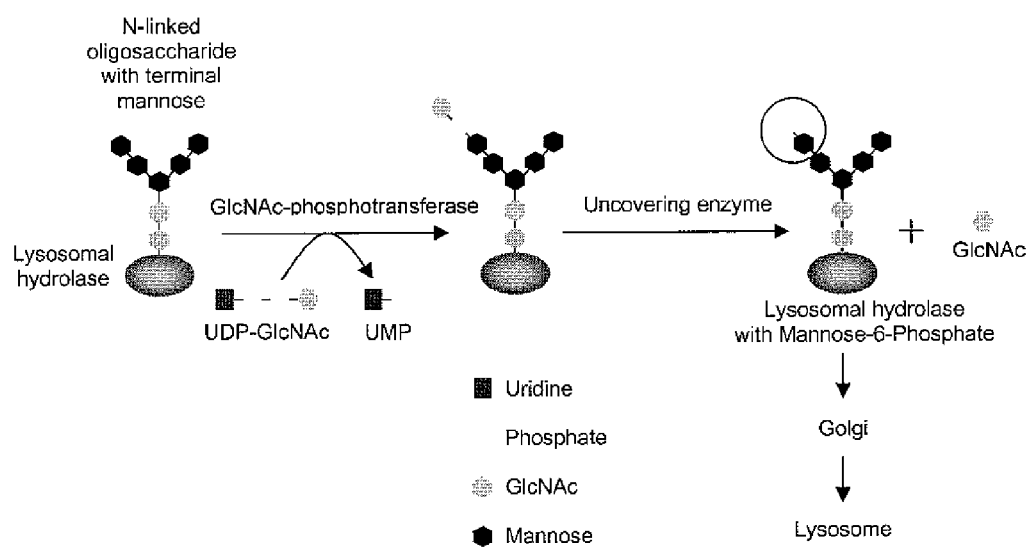

Figure 1.

```
TTTTTCACCAGGACCGCCTGGCTAGCCCTCACCCTGGCGCTGGCCTTCCT  1400
CCTGCTGATCAGCACTGCAGCAAACCTGTCCTTGCTCCTGTCCAGAGCAG  1450
AGAGGAACCGGCGCCTGCATGGGGACTATGCATACCACCCGCTGCAGGAG  1500
ATGAACGGGGAGCCTCTGGCCGCAGAGAAGGAGCAGCCAGGGGGCGCCCA  1550
CAACCCCTTCAAGGACTGAagcctcaagctgcccggggtggcacgtcgcg  1600
aaagcttgtttccccacggtctggcttctgcaggggaaatttcaaggcca  1650
ctggcgtggaccatctgggtgtcctcagcccctgtggggcagccaagttc  1700
ctgatagcacttgtgcctcagcccctcacctggccacctgccagggcacc  1750
tgcaaccctagcaataccatgctcgctggagaggctcagctgcctgcttc  1800
tggcctgcctgtgtctgctgccgagaagcccgtgccccgggagggctgc  1850
cgcactgccaaagagtctccctcctctggggaaggggctgccaacgaac  1900
cagactcagTGAccacgtcatgacagaacagcacatcctggccagcaccc  1950
```

Figure 3A gcggccgcggcgcggagccgagcgggcgtccgtcgccggagctgcaatga
gcggcgcccggaggctgtgacctgcgcgcggcggcccgaccggggcccct
gaatggcggctcgctgaggcggcggcggcggcggcggcggctcaggctcc
tcggggcgtggcgtggcggtgaaggggtgATGCTGTTCAAGCTCCTGCAG
AGACAGACCTATACCTGCCTGTCCCACAGGTATGGGCTCTACGTGTGCTT
CTTGGGCGTCGTTGTCACCATCGTCTCCGCCTTCCAGTTCGGAGAGGTGG
TTCTGGAATGGAGCCGAGATCAATACCATGTTTTGTTTGATTCCTATAGA
GACAATATTGCTGGAAAGTCCTTTCAGAATCGGCTTTGTCTGCCCATGCC
GATTGACGTTGTTACACCTGGGTGAATGGCACAGATCTTGAACTACTGA
AGGAACTACAGCAGGTCAGAGAACAGATGGAGGAGGAGCAGAAAGCAATG
AGAGAAATCCTTGGGAAAAACAACGGAACCTACTAAGAAGAGTGAGAA
GCAGTTAGAGTGTTTGCTAACACACTGCATTAAGGTGCCAATGCTTGTCC
TGGACCCAGCCCTGCCAGCCAACATCACCCTGAAGGACCTGCCATCTCTT
TATCCTTCTTTTCATTCTGCCAGTGACATTTTCAATGTTGCAAAACCAAA
AAACCCTTCTACCAATGTCTCAGTTGTTGTTTTGACAGTACTAAGGATG
TTGAAGATGCCCACTCTGGACTGCTTAAAGGAAATAGCAGACAGACAGTA
TGGAGGGGCTACTTGACAACAGATAAAGAAGTCCCTGGATTAGTGCTAAT
GCAAGATTTGGCTTTCCTGAGTGGATTTCCACCAACATTCAAGGAAACAA
ATCAACTAAAACAAAATTGCCAGAAAATCTTTCCTCTAAAGTCAAACTG
TTGCAGTTGTATTCAGAGGCCAGTGTAGCGCTTCTAAAACTGAATAACCC
CAAGGATTTTCAAGAATTGAATAAGCAAACTAAGAAGAACATGACCATTG
ATGGAAAAGAACTGACCATAAGTCCTGCATATTTATTATGGGATCTGAGC
GCCATCAGCCAGTCTAAGCAGGATGAAGACATCTCTGCCAGTCGTTTTGA
           c.961 A>G
AGATAACGAAGAACTGAGGTACTCATTGCGATCTATCGAGAGGCATGCAC
CATGGGTTCGGAATATTTTCATTGTCACCAACGGGCAGATTCCATCCTGG
CTGAACCTTGACAATCCTCGAGTGACAATAGTAACACACCAGGATGTTTT
TCGAAATTTGAGCCACTTGCCTACCTTTAGTTCACCTGCTATTGAAAGTC
ACATTCATCGCATCGAAGGGCTGTCCCAGAAGTTTATTTACCTAAATGAT
GATGTCATGTTTGGGAAGGATGTCTGGCCAGATGATTTTTACAGTCACTC
CAAAGGCCAGAAGGTTTATTTGACATGGCCTGTGCCAAACTGTGCCGAGG
GCTGCCCAGGTTCCTGGATTAAGGATGGCTATTGTGACAAGGCTTGTAAT
                                   c.1363 G>T
AATTCAGCCTGCGATTGGGATGGTGGGGATTGCTCTGGAAACAGTGGAGG
GAGTCGCTATATTGCAGGAGGTGGAGGTACTGGGAGTATTGGAGTTGGAC
AGCCCTGGCAGTTTGGTGGAGGAATAAACAGTGTCTCTTACTGTAATCAG
GGATGTGCGAATTCCTGGCTCGCTGATAAGTTCTGTGACCAAGCATGCAA
TGTCTTGTCCTGTGGGTTTGATGCTGGCGACTGTGGCAAGATCATTTTC
ATGAATTGTATAAAGTGATCCTTCTCCCAAACCAGACTCACTATATTATT
CCAAAAGGTGAATGCCTGCCTTATTTCAGCTTTGCAGAAGTAGCCAAAAG
AGGAGTTGAAGGTGCCTATAGTGACAATCCAATAATTCGACATGCTTCTA
TTGCCAACAAGTGGAAAACCATCCACCTCATAATGCACAGTGGAATGAAT
GCCACCACAATACATTTTAATCTCACGTTTCAAAATACAAACGATGAAGA
GTTCAAAATGCAGATAACAGTGGAGGTGGACACAAGGGAGGGACCAAAAC
c.1875 C>G

Figure 3B

```
TGAATTCTACAGCCCAGAAGGGTTACGAAAATTTAGTTAGTCCCATAACA
CTTCTTCCAGAGGCGGAAATCCTTTTTGAGGATATTCCCAAAGAAAAACG
CTTCCCGAAGTTTAAGAGACATGATGTTAACTCAACAAGGAGAGCCCAGG
AAGAGGTGAAAATTCCCCTGGTAAATATTTCACTCCTTCCAAAAGACGCC
CAGTTGAGTCTCAATACCTTGGATTTGCAACTGGAACATGGAGACATCAC
TTTGAAAGGATACAATTTGTCCAAGTCAGCCTTGCTGAGATCATTTCTGA
TGAACTCACAGCATGCTAAATAAAAATCAAGCTATAATAACAGATGAA
ACAAATGACAGTTTGGTGGCTCCACAGGAAAACAGGTTCATAAAAGCAT
CTTGCCAAACAGCTTAGGAGTGTCTGAAAGATTGCAGAGGTTGACTTTTC
CTGCAGTGAGTGTAAAAGTGAATGGTCATGACCAGGGTCAGAATCCACCC
CTGGACTTGGAGACCACAGCAAGATTTAGAGTGGAAACTCACACCCAAAA
AACCATAGGCGGAAATGTGACAAAAGAAAAGCCCCATCTCTGATTGTTC
CACTGGAAAGCCAGATGACAAAGAAAAGAAATCACAGGGAAAGAAAAA
GAGAACAGTAGAATGGAGGAAATGCTGAAAATCACATAGGCGTTACTGA
AGTGTTACTTGGAAGAAAGCTGCAGCATTACACAGATAGTTACTTGGGCT
TTTTGCCATGGGAGAAAAAAAGTATTTCCAAGATCTTCTCGACGAAGAA
GAGTCATTGAAGACACAATTGGCATACTTCACTGATAGCAAAAATACTGG
GAGGCAACTAAAAGATACATTTGCAGATTCCCTCAGATATGTAAATAAAA
TTCTAAATAGCAAGTTTGGATTCACATCGCGGAAAGTCCCTGCTCACATG
CCTCACATGATTGACCGGATTGTTATGCAAGAACTGCAAGATATGTTCCC
TGAAGAATTTGACAAGACGTCATTTCACAAAGTGCGCCATTCTGAGGATA
TGCAGTTTGCCTTCTCTTATTTTATTATCTCATGAGTGCAGTGCAGCCA
CTGAATATATCTCAAGTCTTTGATGAAGTTGATACAGATCAATCTGGTGT
CTTGTCTGACAGAGAAATCCGAACACTGGCTACCAGAATTCACGAACTGC
CGTTAAGTTTGCAGGATTTGACAGGTCTGGAACACATGCTAATAAATTGC
TCAAAAATGCTTCCTGCTGATATCACGCAGCTAAATAATATTCCACCAAC
TCAGGAATCCTACTATGATCCCAACCTGCCACCGGTCACTAAAAGTCTAG
TAACAAACTGTAAACCAGTAACTGACAAAATCCACAAAGCATATAAGGAC
AAAAACAAATATAGGTTTGAAATCATGGGAGAAGAAGAAATCGCTTTTAA
AATGATTCGTACCAACGTTTCTCATGTGGTTGGCCAGTTGGATGACATAA
GAAAAAACCCTAGGAAGTTTGTTTGCCTGAATGACAACATTGACCACAAT
CATAAAGATGCTCAGACAGTGAAGGCTGTTCTCAGGGACTTCTATGAATC
CATGTTCCCCATACCTTCCCAATTTGAACTGCCAAGAGAGTATCGAAACC
GTTTCCTTCATATGCATGAGCTGCAGGAATGGAGGGCTTATCGAGACAAA
             c.3598 G>A
TTGAAGTTTTGGACCCATTGTGTACTAGCAACATTGATTATGTTTACTAT
ATTCTCATTTTTTGCTGAGCAGTTAATTGCACTTAAGCGGAAGATATTTC
CAGAAGGAGGATACACAAGAAGCTAGTCCCAATCGAATCAGAGTATAG
aagatcttcatttgaaaaccatctacctcagcatttactgagcattttaa
aactcagcttcacagagatgtctttgtgatgtgatgcttagcagtttggc
ccgaagaaggaaaatatccagtaccatgctgttttgtggcatgaatatag
cccactgaccaggaattatttaaccacccactgaaaacttgtgtgttga
gcagctctgaactgattttacttttaaagaatttgctcatggacctgtca
tccttttttataaaaaggctcactgacaagagacagctgttaatttcccac
agcaatcattgcagactaactttattaggagaagcctatgccagctggga
gtgattgctaagaggctccagtctttgcattccaaagccttttgctaaag
```

Figure 4

MLFKLLQRQTYTCLSHRYGLYVCFLGVVVTIVSAFQFGEVVLEWSRDQYH
VLFDSYRDNIAGKSFQNRLCLPMPIDVVYTWVNGTDLELLKELQQVREQM
EEEQKAMREILGKNTTEPTKKSEKQLECLLTHCIKVPMLVLDPALPANIT
LKDLPSLYPSFHSASDIFNVAKPKNPSTNVSVVVFDSTKDVEDAHSGLLK
GNSRQTVWRGYLTTDKEVPGLVLMQDLAFLSGFPPTFKETNQLKTKLPEN
LSSKVKLLQLYSEASVALLKLNNPKDFQELNKQTKKNMTIDGKELTISPA
YLLWDLSAISQSKQDEDISASRFEDNEELRYSLRSIERHAPWVRNIFIVT
                   p.Ser321Gly
NGQIPSWLNLDNPRVTIVTHQDVFRNLSHLPTFSSPAIESHIHRIEGLSQ
KFIYLNDDVMFGKDVWPDDFYSHSKGQKVYLTWPVPNCAEGCPGSWIKDG
YCDKACNNSACDWDGGDCSGNSGGSRYIAGGGGTGSIGVGQPWQFGGGIN
p.Ala455Ser
SVSYCNQGCANSWLADKFCDQACNVLSCGFDAGDCGQDHFHELYKVILLP
NQTHYIIPKGECLPYFSFAEVAKRGVEGAYSDNPIIRHASIANKWKTIHL
IMHSGMNATTIHFNLTFQNTNDEEFKMQITVEVDTREGPKLNSTAQKGYE
                   p.Phe624Leu
NLVSPITLLPEAEILFEDIPKEKRFPKFKRHDVNSTRRAQEEVKIPLVNI
SLLPKDAQLSLNTLDLQLEHGDITLKGYNLSKSALLRSFLMNSQHAKIKN
QAIITDETNDSLVAPQEKQVHKSILPNSLGVSERLQRLTFPAVSVKVNGH
DQGQNPPLDLETTARFRVETHTQKTIGGNVTKEKPPSLIVPLESQMTKEK
KITGKEKENSRMEENAENHIGVTEVLLGRKLQHYTDSYLGFLPWEKKKYF
QDLLDEEESLKTQLAYFTDSKNTGRQLKDTFADSLRYVNKILNSKFGFTS
RKVPAHMPHMIDRIVMQELQDMFPEEFDKTSFHKVRHSEDMQFAFSYFYY
LMSAVQPLNISQVFDEVDTDQSGVLSDREIRTLATRIHELPLSLQDLTGL
EHMLINCSKMLPADITQLNNIPPTQESYYDPNLPPVTKSLVTNCKPVTDK
IHKAYKDKNKYRFEIMGEEEIAFKMIRTNVSHVVGQLDDIRKNPRKFVCL
NDNIDHNHKDAQTVKAVLRDFYESMFPIPSQFELPREYRNRFLHMHELQE
                             p.Glu1200Lys
WRAYRDKLKFWTHCVLATLIMFTIFSFFAEQLIALKRKIFPRRRIHKEAS
PNRIRV

Figure 5A

```
acttcacgtgaccgcgcggcggccgctgcggcgcgATGGCGGCGGGGCTG
GCGCGGCTCCTGTTGCTCCTCGGGCTCTCGGCCGGCGGGCCCGCGCCGGC
         c.11_19dup
AGGTGCAGCGAAGATGAAGGTGGTGGAGGAGCCCAACGCGTTTGGGGTGA
         c.74 C>A
ACAACCCGTTCTTGCCTCAGGCCAGTCGCCTCCAGGCCAAGAGGGATCCT
TCACCCGTGTCTGGACCCGTGCATCTCTTCCGACTCTCGGGCAAGTGCTT
CAGCCTGGTGGAGTCCACGTACAAGTATGAGTTCTGCCCGTTCCACAACG
TGACCCAGCACGAGCAGACCTTCCGCTGGAACGCCTACAGTGGGATCCTC
GGCATCTGGCACGAGTGGGAGATCGCCAACAACACCTTCACGGGCATGTG
GATGAGGGACGGTGACGCCTGCCGTTCCCGGAGCCGGCAGAGCAAGGTGG
AGCTGGCGTGTGGAAAAGCAACCGGCTGGCCCATGTGTCCGAGCCGAGC
ACCTGCGTCTACGCGCTGACGTTCGAGACCCCCCTCGTCTGCCACCCCCA
CGCCTTGCTAGTGTACCCAACCCTGCCAGAGGCCCTGCAGCGGCAGTGGG
ACCAGGTAGAGCAGGACCTGGCCGATGAGCTGATCACCCCCCAGGGCCAT
GAGAAGTTGCTGAGGACACTTTTTGAGGATGCTGGCTACTTAAAGACCCC
AGAAGAAAATGAACCCACCCAGCTGGAGGGAGGTCCTGACAGCTTGGGGT
              c.688 C>G
TTGAGACCCTGGAAAACTGCAGGAAGGCTCATAAAGAACTCTCAAAGGAG
ATCAAAAGGCTGAAAGGTTTGCTCACCCAGCACGGCATCCCCTACACGAG
GCCCACAGAAACTTCCAACTTGGAGCACTTGGGCCACGAGACGCCCAGAG
CCAAGTCTCCAGAGCAGCTGCGGGGTGACCCAGGACTGCGTGGGAGTTTG
TGAccttgtggtgggagagcagaggtggacgcggccgagagccctacaga
gaagctggctggtaggacccgcagggaccagctgaccaggcttgtgctca
gagaagcagacaaaacaaagattcaaggttttaattaattcccatactga
taaaaataactccatgaattctgtaaaccattgcataaatgctatagtgt
aaaaaatttaaacaagtgttaactttaaacagttcgctacaagtaaatg
attataaatacta
```

Figure 5B

```
MAAGLARLLLLLGLSAGGPAPAGAAKMKVVEEPNAFGVNNPFLPQASRLQ
p.Leu5_Arg7dup    p.Ala25Glu
AKRDPSPVSGPVHLFRLSGKCFSLVESTYKYEFCPFHNVTQHEQTFRWNA
YSGILGIWHEWEIANNTFTGMWRDGDACRSRSQSKVELACGKSNRLAH
VSEPSTCVYALTFETPLVCHPHALLVYPTLPEALQRQWDQVEQDLADELI
TPQGHEKLLRTLFEDAGYLKTPEENEPTQLEGGPDSLGFETLENCRKAHK
                       p.Leu230Val
ELSKEIKRLKGLLTQHGIPYTRPTETSNLEHLGH ETPRAKSPEQLRGDP
GLRGSL
```

Figure 6A gacccgaggccccggtccaatATGGCGACCTCCACGGGTCGCTGGCTTCT
CCTCCGGCTTGCACTATTCGGCTTCCTCTGGGAAGCGTCCGGCGGCCTCG
ACTCGGGGGCCTCCCGCGACGACGACTTGCTACTGCCCTATCCACGCGCG
CGCGCGCCTCCCCGGGACTGCACACGGGTGCGCGCCGGCAACCGCGA
GCACGAGAGTTGGCCTCCGCCTCCCGCGACTCCCGGCGCCGGCGGTCTGG
CCGTGCGCACCTTCGTGTCGCACTTCAGGGACCGCGCGGTGGCCGGCCAC
                  c.252 C>G
CTGACGCGGGCCGTTGAGCCCCTGCGCACCTTCTCGGTGCTGGAGCCCGG
TGGACCCGGCGGCTGCGCGGCGAGACGACGCGCCACCGTGGAGGAGACGG
CGCGGGCGGCCGACTGCCGTGTCGCCCAGAACGGCGGCTTCTTCCGCATG
AACTCGGGCGAGTGCCTGGGGAACGTGGTGAGCGACGAGCGGCGGGTGAG
CAGCTCCGGGGGGCTGCAGAACGCGCAGTTCGGGATCCGCCGCGACGGGA
CCCTGGTCACCGGGTACCTGTCTGAGGAGGAGGTGCTGGACACTGAGAAC
CCATTTGTGCAGCTGCTGAGTGGGGTCGTGTGGCTGATTCGTAATGGAAG
CATCTACATCAACGAGAGCCAAGCCACAGAGTGTGACGAGACACAGGAGA
CAGGTTCCTTTAGCAAATTTGTGAATGTGATATCAGCCAGGACGGCCATT
GGCCACGACCGGAAAGGGCAGCTGGTGCTCTTTCATGCAGACGGCCAAAC
GGAGCAGCGTGGCATCAACCTGTGGGAAATGGCGGAGTTCCTGCTGAAAC
AGGACGTGGTCAACGCCATCAACCTGGATGGGGGTGGCTCTGCCACCTTT
GTGCTCAACGGGACCTTGGCCAGTTACCCGTCAGATCACTGCCAGGACAA
CATGTGGCGCTGTCCCCGCCAAGTGTCCACCGTGGTGTGTGTGCACGAAC
CCCGCTGCCAGCCGCCTGACTGCCACGGCCACGGGACCTGCGTGGACGGG
c.982 C>T
CACTGCCAATGCACCGGGCACTTCTGGCGGGGTCCCGGCTGTGATGAGCT
GGACTGTGGCCCCTCTAACTGCAGCCAGCACGGACTGTGCACGGAGACCG
GCTGCCGCTGTGATGCCGGATGGACCGGGTCCAACTGCAGTGAAGAGTGT
CCCCTTGGCTGGCATGGGCCGGGCTGCCAGAGGCCTTGTAAGTGTGAGCA
CCATTGTCCCTGTGACCCCAAGACTGGCAACTGCAGCGTCTCCAGAGTAA
AGCAGTGTCTCCAGCCACCTGAAGCCACCCTGAGGGCGGGAGAACTCTCC
TTTTTCACCAGGACCGCCTGGCTAGCCCTCACCCTGGCGCTGGCCTTCCT
CCTGCTGATCAGCACTGCAGCAAACCTGTCCTTGCTCCTGTCCAGAGCAG
AGAGGAACCGGCGCCTGCATGGGGACTATGCATACCACCCGCTGCAGGAG
ATGAACGGGGAGCCTCTGGCCGCAGAGAAGGAGCAGCCAGGGGGCGCCCA
CAACCCCTTCAAGGACTGAagcctcaagctgcccggggtggcacgtcgcg
c.1538_1553del

Figure 6B

```
aaagcttgtttccccacggtctggcttctgcaggggaaatttcaaggcca
ctggcgtggaccatctgggtgtcctcagcccctgtggggcagccaagttc
ctgatagcacttgtgcctcagcccctcacctggccacctgccagggcacc
tgcaaccctagcataccatgctcgctggagaggctcagctgcctgcttc
tggcctgcctgtgtctgctgccgagaagcccgtgccccgggagggctgc
cgcactgccaaagagtctcctcctcctggggaaggggctgccaacgaac
cagactcagtgaccacgtcatgacagaacagcacatcctggccagcaccc
ctggctggagtgggttaaagggacgagtctgccttcctggctgtgacacg
ggaccccttttctacagacctcatcactggatttgccaactagaattcga
tttcctgtcataggaagctccttggaagaagggatgggggatgagatca
tgtttacagacctgttttgtcatcctgctgccaagaagttttttaatcac
```

Figure 7

MATSTGRWLLLRLALFGFLWEASGGLDSGASRDDDLLLPYPRARARLPRD
CTRVRAGNREHESWPPPPATPGAGGLAVRTFVSHFRDRAVAGHLTRAVEP
                              p.His84Gln
LRTFSVLEPGGPGGCAARRRATVEETARAADCRVAQNGGFFRMNSGECLG
NVVSDERRVSSSGGLQNAQFGIRRDGTLVTGYLSEEEVLDTENPFVQLLS
GVVWLIRNGSIYINESQATECDETQETGSFSKFVNVISARTAIGHDRKGQ
LVLFHADGQTEQRGINLWEMAEFLLKQDVVNAINLDGGGSATFVLNGTLA
SYPSDHCQDNMWRCPRQVSTVVCVHEPRCQPPDCHGHGTCVDGHCQCTGH
                              p.Arg328Cys
FWRGPGCDELDCGPSNCSQHGLCTETGCRCDAGWTGSNCSEECPLGWHGP
GCQRPCKCEHHCPCDPKTGNCSVSRVKQCLQPPEATLRAGELSFFTRTAW
LALTLALAFLLLISTAANLSLLLSRAERNRRLHGDYAYHPLQEMNGEPLA
AEKEQPGGAHNPFKD
p.Phe513SerfsX113

Figure 8

AGGATGAAGACATCTCTGCCGGTCGTTTTGAAGATAACGA (SEQ ID NO: 1)

AGGATGGCTATTGTGACAAGTCTTGTAATAATTCAGCCTG (SEQ ID NO: 2)

AATACAAACGATGAAGAGTTGAAAATGCAGATAACAGTGG (SEQ ID NO: 3)

TTCATATGCATGAGCTGCAGAAATGGAGGGCTTATCGAGA (SEQ ID NO: 4)

QSKQDEDISAGRFEDNEELR (SEQ ID NO: 5)

SWIKDGYCDKSCNNSACDWD (SEQ ID NO: 6)

LTFQNTNDEELKMQITVEVD (SEQ ID NO: 7)

NRFLHMHELQKWRAYRDKLK (SEQ ID NO: 8)

Figure 9 ggcgcgATGGCGGCGGGGCTGGCGCGGCTGGCGCGGCTCCTGTTGCTCC
(SEQ ID NO: 9)

GCCCGCGCCGGCAGGTGCAGAGAAGATGAAGGTGGTGGAG
(SEQ ID NO: 10)

AAGAAAATGAACCCACCCAGGTGGAGGGAGGTCCTGACAG
(SEQ ID NO: 11)

MAAGLARLARLLLLLGLSAGGPAPAGAAKMKVVEEPN
(SEQ ID NO: 12)

MAAGLARLLLLLGLSAGGPAPAGAEKMKVVEEPN
(SEQ ID NO: 13)

KTPEENEPTQVEGGPDSLGF
(SEQ ID NO: 14)

Figure 10

GTGCGCACCTTCGTGTCGCAGTTCAGGGACCGCGCGGTGG (SEQ ID NO: 15)

TGGTGTGTGTGCACGAACCCTGCTGCCAGCCGCCTGACTG
(SEQ ID NO: 16)

CCCACAACCCCTcaagctgcccggggtggcacgtcgcg
(SEQ ID NO: 17)

GGLAVRTFVSQFRDRAVAGH (SEQ ID NO: 18)

VSTVVCVHEPCCQPPDCHGH (SEQ ID NO: 19)

GEPLAAEKEQPGGAHNPSSCPGWHV
(SEQ ID NO: 20)

Figure 11A

| Genes | No. of exons | Fragment Name | PCR primers (5'→ 3') | Sequencing primers (5'→ 3') |
|---|---|---|---|---|
| GNPTAB | 21 | 5'UTR 2 | FWD: CTGGGCTCCCAGACTCCT (SEQ ID NO: 21) REV: AGTTCTGAGGTCTTTTCAAGCA (SEQ ID NO: 22) | FWD: CTGGGCTCCCAGACTCCT (SEQ ID NO: 129) REV: AGTTCTGAGGTCTTTTCAAGCA (SEQ ID NO: 130) |
| | | 5'UTR 3 | FWD: TCCTGTTGAGTGGCAGATGT (SEQ ID NO: 23) REV: ATCCTTTCCTTGGTGCCTCT (SEQ ID NO: 24) | FWD: TCCTGTTGAGTGGCAGATGT (SEQ ID NO: 131) REV: ATCCTTTCCTTGGTGCCTCT (SEQ ID NO: 132) |
| | | 5'UTR 4 | FWD: AATGCTTTGAATGATGGCAAC (SEQ ID NO: 25) REV: TCGAGACTGTGCCATAGACG (SEQ ID NO: 26) | FWD: AATGCTTTGAATGATGGCAAC (SEQ ID NO: 133) REV: TCGAGACTGTGCCATAGACG (SEQ ID NO: 134) |
| | | 5'UTR 5 | FWD: CACCTTCCCTATGCCCCTCCGTCCTC (SEQ ID NO: 27) REV: CAGGAGCTTGAACAGCATCA (SEQ ID NO: 28) | FWD: GGAAAGGAGCCACATACAGC (SEQ ID NO: 135) REV: CAGGAGCTTGAACAGCATCA (SEQ ID NO: 136) |
| | | Exon 1 | FWD: CTATGCCCCTCCGTCCTC (SEQ ID NO: 29) REV: AATCACATACATGCCTTTTTCCAGTTCT (SEQ ID NO: 30) | FWD: CTATGCCCCTCCGTCCTC (SEQ ID NO: 137) REV: ATCACATACATGCCTTTTTCCAGTTCT (SEQ ID NO: 138) |
| | | Exon 2 | FWD: TTCACCTGGATCTAACACGATG (SEQ ID NO: 31) REV: TCAGATGGGCATACTCCTGA (SEQ ID NO: 32) | FWD: TTCACCTGGATCTAACACGATG (SEQ ID NO: 139) REV: TCAGATGGGCATACTCCTGA (SEQ ID NO: 140) |
| | | Exon 3 | FWD: TGTCATGGTTGGATTACTTCTTCA (SEQ ID NO: 33) REV: TCAGTTTTACCAGATCCTTTTGT (SEQ ID NO: 34) | FWD: TGTCATGGTTGGATTACTTCTTCA (SEQ ID NO: 141) REV: TCAGTTTTACCAGATCCTTTTGT (SEQ ID NO: 142) |
| | | Exon 4 | FWD: CAGCCTGGTACCATGTTTTACT (SEQ ID NO: 35) REV: TGTACCTAATTTGGGGTCAAAAA (SEQ ID NO: 36) | FWD: CAGCCTGGTACCATGTTTTACT (SEQ ID NO: 143) REV: TGTACCTAATTTGGGGTCAAAAA (SEQ ID NO: 144) |
| | | Exon 5 | FWD: TCCATGAGATAAAAGTCTTCATTTG (SEQ ID NO: 37) REV: TGTTTTGCTTCTCTTTGTGCAT (SEQ ID NO: 38) | FWD: TCCATGAGATAAAAGTCTTCATTTG (SEQ ID NO: 145) REV: TGTTTTGCTTCTCTTTGTGCAT (SEQ ID NO: 146) |
| | | Exon 6 | FWD: TTTTGTCTCCTTCAGCTTCCTT (SEQ ID NO: 39) REV: GCATCACAACACAAGCTTCAA (SEQ ID NO: 40) | FWD: TTTTGTCTCCTTCAGCTTCCTT (SEQ ID NO: 147) REV: GCATCACAACACAAGCTTCAA (SEQ ID NO: 148) |
| | | Exon 7 | FWD: GCTGTTTTTCTTTGAGAATCTTTTT (SEQ ID NO: 41) REV: TGGCAGAACAGAATCCCTCT (SEQ ID NO: 42) | FWD: GCTGTTTTTCTTTGAGAATCTTTTT (SEQ ID NO: 149) REV: TGGCAGAACAGAATCCCTCT (SEQ ID NO: 150) |
| | | Exon 8 | FWD: TGAGGTGAGCAGAGATCGTG (SEQ ID NO: 43) REV: TACCAAACCAATGGCAGTGA (SEQ ID NO: 44) | FWD: TGAGGTGAGCAGAGATCGTG (SEQ ID NO: 151) REV: TACCAAACCAATGGCAGTGA (SEQ ID NO: 152) |
| | | Exon 9 | FWD: TGCTGTCTCTTTGAATTTTGG (SEQ ID NO: 45) REV: AGGAAGGGAAGGCAATGAAG (SEQ ID NO: 46) | FWD: TGCTGTCTCTTTGAATTTTGG (SEQ ID NO: 153) REV: AGGAAGGGAAGGCAATGAAG (SEQ ID NO: 154) |
| | | Exon 10 | FWD: CCCTTTACCCTTCTACCTCCA (SEQ ID NO: 47) REV: TATGCTTCCCAAGCTGGTCT (SEQ ID NO: 48) | FWD: CCCTTTACCCTTCTACCTCCA (SEQ ID NO: 155) REV: TATGCTTCCCAAGCTGGTCT (SEQ ID NO: 156) |
| | | Exon 11 | FWD: TCAACGCAGCAGGATCTAAA (SEQ ID NO: 49) REV: AGGTTTGCACCACCACACTT (SEQ ID NO: 50) | FWD: TCAACGCAGCAGGATCTAAA (SEQ ID NO: 157) REV: AGGTTTGCACCACCACACTT (SEQ ID NO: 158) |
| | | Exon 12 | FWD: AGGTGATCCAGCCTCCTCTG (SEQ ID NO: 51) REV: GAATGCAAGGCTGGTAAAGG (SEQ ID NO: 52) | FWD: AGGTGATCCAGCCTCCTCTG (SEQ ID NO: 159) REV: GAATGCAAGGCTGGTAAAGG (SEQ ID NO: 160) |

Figure 11B

| Genes | No. of exons | Fragment Name | PCR primers (5'→ 3') | Sequencing primers (5'→ 3') |
|---|---|---|---|---|
| | | Exon 13_1 | FWD: CAAGGACGACATGCAAATTC (SEQ ID NO: 53) REV: GCGTCTTTTGGAAGGAGTGA (SEQ ID NO: 54) | FWD: CAAGGACGACATGCAAATTC (SEQ ID NO: 161) REV: GCGTCTTTTGGAAGGAGTGA (SEQ ID NO: 162) |
| | | Exon 13_2 | FWD: TACAGCCCAGAAGGGTTACG (SEQ ID NO: 55) REV: AATCAGAGATGGGGGCTTTT (SEQ ID NO: 56) | FWD: TACAGCCCAGAAGGGTTACG (SEQ ID NO: 163) REV: AATCAGAGATGGGGGCTTTT (SEQ ID NO: 164) |
| | | Exon 13_3 | FWD: TGCAGAGGTTGACTTTTCCTG (SEQ ID NO: 57) REV: TCACACTTGGGCTGTTTCCT (SEQ ID NO: 58) | FWD: TGCAGAGGTTGACTTTTCCTG (SEQ ID NO: 165) REV: TCACACTTGGGCTGTTTCCT (SEQ ID NO: 166) |
| | | Exon 14 | FWD: TTTGCTCCTAATGAAGAGTTCG (SEQ ID NO: 59) REV: CTTCAGGGAACCTGTCCAAA (SEQ ID NO: 60) | FWD: TTTGCTCCTAATGAAGAGTTCG (SEQ ID NO: 167) REV: CTTCAGGGAACCTGTCCAAA (SEQ ID NO: 168) |
| | | Exon 15 | FWD: CGTGTTTGAGTTGTTTGCTTG (SEQ ID NO: 61) REV: GCTCAGCTGCCTCAGCAT (SEQ ID NO: 62) | FWD: CGTGTTTGAGTTGTTTGCTTG (SEQ ID NO: 169) REV: GCTCAGCTGCCTCAGCAT (SEQ ID NO: 170) |
| | | Exon 16 | FWD: TGGGTATCTCAGAGGCCAGA (SEQ ID NO: 63) REV: AACAGGACATCCGCTTATGG (SEQ ID NO: 64) | FWD: TGGGTATCTCAGAGGCCAGA (SEQ ID NO: 171) REV: AACAGGACATCCGCTTATGG (SEQ ID NO: 172) |
| | | Exon 17 | FWD: TTGGTGTTTTTCTTACCTCCAGA (SEQ ID NO: 65) REV: CCGTAGTGGACTCAACATCCA (SEQ ID NO: 66) | FWD: TTGGTGTTTTTCTTACCTCCAGA (SEQ ID NO: 173) REV: CCGTAGTGGACTCAACATCCA (SEQ ID NO: 174) |
| | | Exon 18 | FWD: TAAAATTTATATGAGATTGTTTGCTG (SEQ ID NO: 67) REV: ACTCAACCACCAGCTCCAAC (SEQ ID NO: 68) | FWD: AAAATTTATATGAGATTGTTTGCTG (SEQ ID NO: 175) REV: ACTCAACCACCAGCTCCAAC (SEQ ID NO: 176) |
| | | Exon 19 | FWD: TCATTCCCCCAGAGAATCAT (SEQ ID NO: 69) REV: AGCTTGGGCAACAAGAACAA (SEQ ID NO: 70) | FWD: TCATTCCCCCAGAGAATCAT (SEQ ID NO: 177) REV: AGCTTGGGCAACAAGAACAA (SEQ ID NO: 178) |
| | | Exon 20 | FWD: TTGCAAGACAATGTTTTTGTG (SEQ ID NO: 71) REV: TTGCTGCCTGAATATTGTGAA (SEQ ID NO: 72) | FWD: TTGCAAGACAATGTTTTTGTG (SEQ ID NO: 179) REV: TTGCTGCCTGAATATTGTGAA (SEQ ID NO: 180) |
| | | Exon 21 | FWD: TGGAAGAGGAATGATGGAGATT (SEQ ID NO: 73) REV: GGAGCCTCTTAGCAATCACTC (SEQ ID NO: 74) | FWD: TGGAAGAGGAATGATGGAGATT (SEQ ID NO: 181) REV: GGAGCCTCTTAGCAATCACTC (SEQ ID NO: 182) |
| | | 3'UTR 1 | FWD: GCTCATGGACCTGTCATCCT (SEQ ID NO: 75) REV: CAGTGCCATCAGCACTACTCA (SEQ ID NO: 76) | FWD: GCTCATGGACCTGTCATCCT (SEQ ID NO: 183) REV: CAGTGCCATCAGCACTACTCA (SEQ ID NO: 184) |
| | | 3'UTR 2 | FWD: GACTTCAGCCCCTAAGAATGC (SEQ ID NO: 77) REV: AGGCTGAGACAGAACTGCTTG (SEQ ID NO: 78) | FWD: GACTTCAGCCCCTAAGAATGC (SEQ ID NO: 185) REV: AGGCTGAGACAGAACTGCTTG (SEQ ID NO: 186) |
| | | 3'UTR 3 | FWD: GACCCTCAGGCCATCATTT (SEQ ID NO: 79) REV: TCAGCACAGAACCTGATACACA (SEQ ID NO: 80) | FWD: GACCCTCAGGCCATCATTT (SEQ ID NO: 187) REV: TCAGCACAGAACCTGATACACA (SEQ ID NO: 188) |

Figure 11C

| Genes | No. of exons | Fragment Name | PCR primers (5'→ 3') | Sequencing primers (5'→ 3') |
|---|---|---|---|---|
| GNPTAG | 11 | 5'UTR 1 | FWD: TCACCGATCTCCTCCTCCT (SEQ ID NO: 81) REV: TGCCCAGAGAATCCTCCTTA (SEQ ID NO: 82) | FWD: TCACCGATCTCCTCCTCCT (SEQ ID NO: 189) REV: TGCCCAGAGAATCCTCCTTA (SEQ ID NO: 190) |
| | | 5'UTR 2 | FWD: TTGCTGCGAAACAAACATTC (SEQ ID NO: 83) REV: GAGACACCGTTTGGGAAGAT (SEQ ID NO: 84) | FWD: TTGCTGCGAAACAAACATTC (SEQ ID NO: 191) REV: GAGACACCGTTTGGGAAGAT (SEQ ID NO: 192) |
| | | 5'UTR 3 | FWD: CCATAGTTCACGGGGTTGG (SEQ ID NO: 85) REV: CCCGAGGTCGTCTTCATTT (SEQ ID NO: 86) | FWD: CCATAGTTCACGGGGTTGG (SEQ ID NO: 193) REV: CCCGAGGTCGTCTTCATTT (SEQ ID NO: 194) |
| | | 5'UTR 4 | FWD: GCAACGGAGGCAAACTAGAC (SEQ ID NO: 87) REV: GAGAGCGGGTCAGGGTTT (SEQ ID NO: 88) | FWD: GCAACGGAGGCAAACTAGAC (SEQ ID NO: 195) REV: GAGAGCGGGTCAGGGTTT (SEQ ID NO: 196) |
| | | Exon 1 | FWD: AGGCCCTCAAACCCTGAC (SEQ ID NO: 89) REV: TCCTCCACCACCTTCATCTT (SEQ ID NO: 90) | FWD: AGGCCCTCAAACCCTGAC (SEQ ID NO: 197) REV: TCCTCCACCACCTTCATCTT (SEQ ID NO: 198) |
| | | Exon 2 | FWD: GTTGCTCCTCGGGCTCTC (SEQ ID NO: 91) REV: AAGGCTGACAAACCAATGCT (SEQ ID NO: 92) | FWD: GTTGCTCCTCGGGCTCTC (SEQ ID NO: 199) REV: AAGGCTGACAAACCAATGCT (SEQ ID NO: 200) |
| | | Exon 3 | FWD: AAGATGAAGGTGGTGGAGGA (SEQ ID NO: 93) REV: ACCTCTCGGAAAGGAAAGGA (SEQ ID NO: 94) | FWD: AAGATGAAGGTGGTGGAGGA (SEQ ID NO: 201) REV: ACCTCTCGGAAAGGAAAGGA (SEQ ID NO: 202) |
| | | Exon 4 & 5 | FWD: CAGACTCTGCCAGTCTTTGC (SEQ ID NO: 95) REV: CTCCCACTCGTGCCAGAT (SEQ ID NO: 96) | FWD: CAGACTCTGCCAGTCTTTGC (SEQ ID NO: 203) REV: CTCCCACTCGTGCCAGAT (SEQ ID NO: 204) |
| | | Exon 6 & 7 | FWD: GTGGGATCCTCGGGTGAGT (SEQ ID NO: 97) REV: CAAGAGAAGCCAGGCTCAG (SEQ ID NO: 98) | FWD: AGGGATCCCAAAGCAGCA (SEQ ID NO: 205) REV: ACCCCACTGGGCTCAACT (SEQ ID NO: 206) |
| | | Exon 8 | FWD: AGCTGAGCCTGGCTTCTCTT (SEQ ID NO: 99) REV: GCCAGCATCCTCAAAAAGTG (SEQ ID NO: 100) | FWD: AGCTGAGCCTGGCTTCTCTT (SEQ ID NO: 207) REV: GCCAGCATCCTCAAAAAGTG (SEQ ID NO: 208) |
| | | Exon 9 & 10 | FWD: CAGGACCTGGCCGATGAG (SEQ ID NO: 101) REV: AGTTTCTGCCAAAACACCAG (SEQ ID NO: 102) | FWD: CAGGACCTGGCCGATGAG (SEQ ID NO: 209) REV: AGTTTCTGCCAAAACACCAG (SEQ ID NO: 210) |
| | | Exon 11 | FWD: TACACGAGGCCCACAGGT (SEQ ID NO: 103) REV: TTATTTGAATGGAATTTTCTTAACC (SEQ ID NO: 104) | FWD: TACACGAGGCCCACAGGT (SEQ ID NO: 211) REV: TTATTTGAATGGAATTTTCTTAACC (SEQ ID NO: 212) |

Figure 11D

| Genes | No. of exons | Fragment Name | PCR primers (5'→ 3') | Sequencing primers (5'→ 3') |
|---|---|---|---|---|
| NAGPA | 10 | 5'UTR 1 | FWD: CCAGAAGTGCTGACTGTGGA (SEQ ID NO: 105) REV: AGGTGATCCGCCTCCTTC (SEQ ID NO: 106) | FWD: CCAGAAGTGCTGACTGTGGA (SEQ ID NO: 213) REV: AGGTGATCCGCCTCCTTC (SEQ ID NO: 214) |
| | | 5'UTR 2 | FWD: TGCACAGGCAGTTTTACTGG (SEQ ID NO: 107) REV: TGATACTGTTGCGGTCTTGC (SEQ ID NO: 108) | FWD: TGCACAGGCAGTTTTACTGG (SEQ ID NO: 215) REV: TGATACTGTTGCGGTCTTGC (SEQ ID NO: 216) |
| | | 5'UTR 3 | FWD: CCTTGTGTCCACGCTCCTTA (SEQ ID NO: 109) REV: AAGGCTCCTCAGCCTTTTGT (SEQ ID NO: 110) | FWD: CCTTGTGTCCACGCTCCTTA (SEQ ID NO: 217) REV: AAGGCTCCTCAGCCTTTTGT (SEQ ID NO: 218) |
| | | 5'UTR 4 | FWD: GTGTCCCCACGTTTTCATTT (SEQ ID NO: 111) REV: AATTACCTGCGCTCTTTTCG (SEQ ID NO: 112) | FWD: GTGTCCCCACGTTTTCATTT (SEQ ID NO: 219) REV: AATTACCTGCGCTCTTTTCG (SEQ ID NO: 220) |
| | | Exon 1 | FWD: GAGAGTTCTTTATGCTCTCCTTGC (SEQ ID NO: 113) REV: GAGGCCAACTCTCGTGCTC (SEQ ID NO: 114) | FWD: GCTCTCCTTGCAACTTCCTG (SEQ ID NO: 221) REV: GGGCAGTAGCAAGTCGTCGT (SEQ ID NO: 222) |
| | | Exon 2 | FWD: GCACTATTCGGCTTCCTCTG (SEQ ID NO: 115) REV: GCGATTCCTATCCCCATTCT (SEQ ID NO: 116) | FWD: TCCTCTGGGAAGCGTCCGG (SEQ ID NO: 223) REV: GTTAAGTGACTTGAACACGG (SEQ ID NO: 224) |
| | | Exon 3 | FWD: GAATCTAGCAGCCAGGTTGG (SEQ ID NO: 117) REV: ATCTTCCTCCCCATGAATCC (SEQ ID NO: 118) | FWD: AGGTTGGGATGGCTAGGGAG (SEQ ID NO: 225) REV: CTCCCTAGCCATCCCAACCT (SEQ ID NO: 226) |
| | | Exon 4 | FWD: GAGACTGGGATGTGCAGAGG (SEQ ID NO: 119) REV: GGGGGACAGATAGGTGTCAA (SEQ ID NO: 120) | FWD: GGAGACGAGCAAGGAGGCT (SEQ ID NO: 227) REV: CCAGAAAGCAGGTAGAGTCA (SEQ ID NO: 228) |
| | | Exon 5 | FWD: TGGGTGTGATCTCACGTGTT (SEQ ID NO: 121) REV: ACCAACTGACCCTGCTCCTA (SEQ ID NO: 122) | FWD: GCTCTGCACTGTGGAAGGAA (SEQ ID NO: 229) REV: AGGGACTGCAGCAATTTCTG (SEQ ID NO: 230) |
| | | Exon 6 & 7 | FWD: GGTAGACAGGTGAGAATGGAGAG (SEQ ID NO: 123) REV: ACAGTGATGTGCAGGTGAGG (SEQ ID NO: 124) | FWD: GGGCAGCCTGGAGGGAGTT (SEQ ID NO: 231) REV: GAGACAGAAGCAGCAGAGGA (SEQ ID NO: 232) |
| | | Exon 8 & 9 | FWD: ACGTTCAGGGGCTAGTCCAG (SEQ ID NO: 125) REV: GAGGCTGGGCACTCGAAG (SEQ ID NO: 126) | FWD: CAGGTATCCTGTCCTGTCGA (SEQ ID NO: 233) REV: GGAGAGCTGGTCCCGCTTCC (SEQ ID NO: 234) |
| | | Exon 10 | FWD: TCTTAAATGTTGCCCCATCC (SEQ ID NO: 127) REV: CAGCGAGCATGGTATTGCTA (SEQ ID NO: 128) | FWD: ACTGCAGCAAACCTGTCCTT (SEQ ID NO: 235) REV: GGAGGAGGGAGACTCTTTGG (SEQ ID NO: 236) |

DIAGNOSTIC AND THERAPEUTIC USES OF GNPTAB, GNPTG, AND NAGPA IN STUTTERING

CROSS-REFERENCE TO RELATED APPLICATIONS

This patent application is a U.S. National Phase of International Patent Application No. PCT/US2010/23437, filed Feb. 8, 2010, which claims the benefit of U.S. Provisional Patent Application No. 61/150,954, filed Feb. 9, 2009, the entire contents of which are incorporated herein by reference.

BACKGROUND OF THE INVENTION

Stuttering, also known as stammering, is a common speech disorder known since antiquity, affecting all populations and language groups. Stuttering is a disorder of unknown etiology characterized by repetitions, prolongations and interruptions in the flow of speech. Although the underlying causes of stuttering are unknown, substantial evidence from twin studies, adoption studies and family studies support genetic contributions to the etiology of the disorder. Such data have motivated a number of genetic linkage studies that have produced evidence for linkage at numerous loci across the genome (Riaz et al., Am. J. Hum. Genet., 76:647-651 (2005); Wittke-Thompson et al., J. Fluency Disord. 32:33-50 (2007); Suresh et al., Am. J. Hum. Genet., 78:554-563 (2006)). The most statistically significant linkage has been reported on the long arm of chromosome 12, based on the study of a group of consanguineous families in Pakistan (Riaz et al.). However, numerous genome-wide linkage scans performed in stuttering families have failed to identify robust linkage signals (Shugart et al., Suresh et al.). The lack of understanding of the etiology of stuttering has, until now, limited the ability to diagnose and treat this disorder.

BRIEF SUMMARY OF THE INVENTION

In an embodiment, the invention provides an isolated or purified nucleic acid molecule comprising a nucleotide sequence encoding at least one mutated form of the alpha and beta subunits of the enzyme N-acetylglucosamine-1-phosphotransferase "GNPTAB," wherein the presence of the mutation in the genome of a human is associated with stuttering. For example, the mutated form of GNPTAB can comprise specified nucleic acid sequences as described herein. For instance, in an embodiment, the inventive mutated form of GNPTAB comprises one or more of the isolated or purified nucleic acid sequences of SEQ ID NO: 1-4, or an isolated or purified nucleic acid molecule comprising a nucleotide sequence that is complementary to any of SEQ ID NO: 1-4.

In an embodiment, the invention also provides an isolated or purified nucleic acid molecule comprising a nucleotide sequence encoding at least one mutated form of the gamma regulatory subunit of the enzyme N-acetylglucosamine-1-phosphotransferase "GNPTG," wherein the presence of the mutation in the genome of a human is associated with stuttering. For example, the mutated form of GNPTG comprises specified nucleic acid sequences as described herein. For instance, in an embodiment, the inventive mutated form of GNPTG comprises one or more of the isolated or purified sequences of SEQ ID NO: 9-11, or an isolated or purified nucleic acid molecule comprising a nucleotide sequence that is complementary to any of SEQ ID NO: 9-11

In addition, in another embodiment, the invention also provides an isolated or purified nucleic acid molecule comprising a nucleotide sequence encoding at least one mutated form of N-acetylglucosamine-1-phosphodiester alpha-n-acetylglucosaminidase "NAGPA" wherein the presence of the mutation in the genome of a human is associated with stuttering. For example, the mutated form of NAGPA can comprise specified nucleic acid sequences as described herein. For instance, in an embodiment, the inventive mutated form of NAGPA comprises one or more of the isolated or purified nucleic acid sequences of SEQ ID NO: 15-17, or an isolated or purified nucleic acid molecule comprising a nucleotide sequence that is complementary to any of SEQ ID NO: 15-17.

The invention further provides related polypeptides and proteins, as well as related nucleic acids, recombinant expression vectors, and host cells. Further provided by the invention are antibodies, and kits containing same.

Methods of detecting stuttering or a predisposition to stuttering in a human, which method comprises detecting at least one mutation in a gene encoding GNPTAB, GNPTG or NAGPA in a test sample comprising a nucleic acid comprising any one or more of the isolated or purified nucleic acid sequences of SEQ ID NO: 1-4, 9-11 and 15-17 obtained from the human, wherein the presence of at least one of these nucleic acid sequences is indicative of stuttering or a predisposition to stuttering in the human are further provided by the invention.

Methods of detecting stuttering or a predisposition to stuttering in a human, which method comprises detecting GNPTAB, GNPTG or NAGPA proteins or fragments thereof, in a test sample comprising any one or more of the isolated or purified polypeptides having the amino acid sequence of SEQ ID NO: 5-8, 12-14 and 18-20 obtained from the human, wherein the presence of at least one of these amino acid sequences is indicative of stuttering or a predisposition to stuttering in the human.

In an embodiment, the present invention provides a method for the treatment of stuttering or a predisposition to stuttering in a human having at least one mutation in a gene encoding any of GNPTAB, GNPTG or NAGPA, by administering a symptom treating amount of a pharmaceutically acceptable composition comprising an isolated or purified wild-type form of any of GNPTAB, GNPTG or NAGPA.

BRIEF DESCRIPTION OF THE SEVERAL VIEWS OF THE DRAWING(S)

FIG. 1 shows a mutated form of exon 10 of the nucleic acid sequence of NAGPA. The p.Phe513SerfsX113 notation denotes a frame shift mutation that changes phenylalanine 513 to serine, and extends the open reading frame 113 amino acids downstream. The 16 base pair deleted region in exon10 of NAGPA gene is underlined, and stop codon positions of wild type and mutant are in bold type. The numbering is based on the cDNA (NM_016256) sequence of NAGPA.

FIG. 2 is a diagrammatic representation of lysosomal enzyme trafficking in a mammalian cell. In the first step, GlcNAc-phosphotransferase (GNPTAB/G) catalyzes the covalent linkage of GlcNAc-1-phosphate from UDP-GlcNAc to terminal mannose residues of N-linked oligosaccharides on enzymes destined for the lysozome. In the second step, N-acetylglucosamine-1-phosphodiester alpha-n-acetylglucosaminidase (NAGPA), also known as the uncovering enzyme, removes a GlcNAc group, thereby exposing mannose-6-phosphate (circled). Enzymes with this targeting signal are then routed through the Golgi to the lysozome.

FIG. 3A-B provides the mRNA sequence for the GNPTAB enzyme as found in Genbank Accession No. NM_024312.

The location of each mutation is identified by their position number, and the nucleotide is underlined. The labels underneath each mutation indicate how the nucleotide is changed from the wild-type.

FIG. 4 provides the translated protein sequence for the GNPTAB enzyme as found in Genbank Accession No. NM_024312. The location of each mutation is identified by their position number, and the amino acid is underlined. The labels underneath each mutation indicate how the amino acid is changed from the wild-type.

FIG. 5A provides the mRNA sequence for the GNPTG enzyme as found in Genbank Accession No. NM_032520. The location of each mutation is identified by their position number, and the nucleotide is underlined. The labels underneath each mutation indicate how the nucleotide is changed from the wild-type.

FIG. 5B provides the translated protein sequence for the GNPTG enzyme as found in Genbank Accession No. NM_032520. The location of each mutation is identified by their position number, and the amino acid is underlined. The labels underneath each mutation indicate how the amino acid is changed from the wild-type.

FIG. 6A-B provides the mRNA sequence for the NAGPA enzyme as found in Genbank Accession No. NM_016256. The location of each mutation is identified by their position number, and the nucleotide is underlined. The labels underneath each mutation indicate how the nucleotide is changed from the wild-type.

FIG. 7 provides the translated protein sequence for the NAGPA enzyme as found in Genbank Accession No. NM_016256. The location of each mutation is identified by their position number, and the amino acid is underlined. The labels underneath each mutation indicate how the amino acid is changed from the wild-type.

FIG. 8 provides nucleotide sequence fragments which contain the mutated codons (underlined) for the GNPTAB gene (SEQ ID NO: 1-4) and the corresponding peptides which contain the mutated amino acids (underlined) (SEQ ID NO: 5-8).

FIG. 9 provides nucleotide sequence fragments which contain the mutated codons (underlined) for the GNPTG gene (SEQ ID NO: 9-11) and the corresponding peptides which contain the mutated amino acids (underlined) (SEQ ID NO: 12-14).

FIG. 10 provides nucleotide sequence fragments which contain the mutated codons (underlined) for the NAGPA gene (SEQ ID NO: 15-17) and the corresponding peptides which contain the mutated amino acids (underlined) (SEQ ID NO: 18-20).

FIG. 11A-D depict a table with the PCR primer sequences and sequencing primer sequences used to identify the mutations in the GNPTAB, GNPTG and NAGPA genes in the various exons listed.

DETAILED DESCRIPTION OF THE INVENTION

In an embodiment, the invention provides an isolated or purified nucleic acid molecule comprising a nucleotide sequence encoding at least one mutated form of the alpha and beta subunits of the enzyme N-acetylglucosamine-1-phosphotransferase "GNPTAB," wherein the presence of the mutation in the genome of a human is associated with stuttering. For example, the mutated form of GNPTAB can comprise specified isolated and purified nucleic acid sequences as described herein. For instance, in an embodiment, the inventive mutated form of GNPTAB comprises any one of the isolated and purified nucleic acid sequences of SEQ ID NO: 1-4, or an isolated or purified nucleic acid molecule comprising a nucleotide sequence that is complementary to any of SEQ ID NO: 1-4.

In an embodiment, the invention also provides an isolated or purified nucleic acid molecule comprising a nucleotide sequence encoding at least one mutated form of the gamma regulatory subunit of the enzyme N-acetylglucosamine-1-phosphotransferase "GNPTG," wherein the presence of the mutation in the genome of a human is associated with stuttering. For example, the mutated form of GNPTG comprises specified nucleic acid sequences as described herein. For instance, in an embodiment, the inventive mutated form of GNPTG comprises any one of the isolated and purified nucleic acid sequences of SEQ ID NO: 9-11, or an isolated or purified nucleic acid molecule comprising a nucleotide sequence that is complementary to any of SEQ ID NO: 9-11

In addition, in another embodiment, the invention also provides an isolated or purified nucleic acid molecule comprising a nucleotide sequence encoding at least one mutated form of N-acetylglucosamine-1-phosphodiester alpha-n-acetylglucosaminidase "NAGPA" wherein the presence of the mutation in the genome of a human is associated with stuttering. For example, the isolated or purified mutated form of NAGPA can comprise specified nucleic acid sequences as described herein. For instance, in an embodiment, the inventive mutated form of NAGPA comprises any one of the isolated or purified nucleic acid sequences of SEQ ID NO: 15-17, or an isolated or purified nucleic acid molecule comprising a nucleotide sequence that is complementary to any of SEQ ID NO: 15-17.

In another embodiment, the invention further provides an isolated or purified protein comprising any one of the polypeptides described herein. By "protein" is meant a molecule comprising one or more polypeptide chains.

In an embodiment, the protein of the invention comprises any one or more of the isolated or purified polypeptide chains described herein. In this regard, the protein of an embodiment of the invention comprises any one of the isolated or purified polypeptides encoded by the above nucleic acids comprising the amino acid sequences of SEQ ID NO: 5-8, 12-14, and 18-20.

Included in the scope of an embodiment of the invention is an isolated or purified nucleic acid molecule comprising a portion of mutated form of GNPTAB, GNPTG or NAGPA corresponding to any one of the isolated or purified sequences identified as SEQ ID NO: 1-4, 9-11, and 15-17, wherein the presence of the mutation in the genome of a human is associated with stuttering or the predisposition for stuttering.

The nucleic acid molecules which correspond to portions of the mutated forms of GNPTAB described above are selected from the group consisting of: the allelic variant at position 961 where an A is substituted by a G codon (SEQ ID NO: 1); the allelic variant at position 1363 where a G is substituted by a T codon (SEQ ID NO: 2); the allelic variant at position 1875 where a C is substituted by a G codon (SEQ ID NO: 3); and the allelic variant at position 3598 where a G is substituted by an A codon (SEQ ID NO: 4).

The isolated or purified nucleic acid molecules which correspond to portions of the mutated forms of GNPTG described above are selected from the group consisting of: the allelic variant at position 11 which is a 9 base pair duplication of the sequence encoded by codons 11-19 (SEQ ID NO: 9); the allelic variant at position 74 where a C is substituted by a A codon (SEQ ID NO: 10); and the allelic variant at position 688 where a C is substituted by a G codon (SEQ ID NO: 11).

The isolated or purified nucleic acid molecules which correspond to portions of the mutated forms of NAGPA described above are selected from the group consisting of: the allelic variant at position 252 where a C is substituted by a G codon (SEQ ID NO: 15); the allelic variant at position 982 where a C is substituted by a T codon (SEQ ID NO: 16); and the allelic variant at position 1538 where there is a 16 base pair deletion (SEQ ID NO: 17).

In one embodiment the isolated or purified nucleic acid molecule consists essentially of a nucleotide sequence encoding the entire GNPTAB enzyme containing any of the mutations or a fragment thereof comprising at least about 5600 contiguous nucleotides (FIGS. 3A, 3B). Alternatively, the isolated or purified nucleic acid molecule consists essentially of any one or more of the isolated or purified nucleotide sequences of SEQ ID NO: 1-4 or an isolated or purified fragment thereof comprising at least about 17 contiguous nucleotides. In one embodiment, the isolated or purified fragment comprises at least about 20 contiguous nucleotides. Further, the isolated or purified nucleic acid molecule can hybridize under stringent conditions to an isolated or purified nucleic acid molecule consisting essentially of the nucleotide sequence that is complementary to any of SEQ ID NO: 1-4 or a fragment thereof.

In another embodiment, the present invention provides an isolated or purified nucleic acid molecule consisting essentially of a nucleotide sequence encoding the entire GNPTG enzyme containing any of the mutations or an isolated or purified fragment comprising at least about 1280 contiguous nucleotides (FIG. 5). Alternatively, the isolated or purified nucleic acid molecule consists essentially of the isolated or purified nucleotide sequence of SEQ ID NO: 9-11 or a f isolated or purified fragment thereof comprising at least about 17 contiguous nucleotides. In one embodiment, the isolated or purified fragment comprises at least about 20 contiguous nucleotides. Further, the isolated or purified nucleic acid molecule can hybridize under stringent conditions to an isolated or purified nucleic acid molecule consisting essentially of the nucleotide sequence that is complementary to any of SEQ ID NO: 9-11 or an isolated or purified fragment thereof.

In another embodiment, the present invention provides an isolated or purified nucleic acid molecule consisting essentially of a nucleotide sequence encoding the entire NAGPA enzyme containing the mutation or an isolated or purified fragment thereof comprising at least 1550 contiguous nucleotides (FIG. 6). Alternatively, the isolated or purified nucleic acid molecule consists essentially of the nucleotide sequence of SEQ ID NO: 15-17 or an isolated or purified fragment thereof comprising at least about 17 contiguous nucleotides. In another embodiment, the fragment comprises at least about 20 contiguous nucleotides. Further, the isolated or purified nucleic acid molecule can hybridize under stringent conditions to an isolated or purified nucleic acid molecule consisting essentially of the nucleotide sequence that is complementary to any of SEQ ID NO: 15-17 or an isolated or purified fragment thereof.

The invention further provides methods for detecting stuttering or a predisposition to stuttering in a human. In one embodiment, the method comprises detecting at least one mutation, such as 961A→G, 1363G→T, 1875C→G or 3598G→A in an isolated or purified nucleic acid molecule comprising a nucleic acid sequence encoding GNPTAB or an isolated or purified fragment thereof, in a test sample, the method comprising forming a complex with an isolated or purified nucleic acid molecule comprising the GNPTAB gene or an isolated or purified fragment thereof, obtained from a human, wherein the presence of at least one mutation is indicative of stuttering or a predisposition to stuttering in a human. In another embodiment, the method comprises detecting at least one mutation, such as 11_19dup, 74C→A, or 688C→G in a gene encoding GNPTG or an isolated or purified fragment thereof in a test sample, comprising forming a complex with an isolated or purified nucleic acid molecule comprising the GNPTG gene or an isolated or purified fragment thereof, obtained from a human, wherein the presence of at least one mutation is indicative of stuttering or a predisposition to stuttering in a human. In yet another embodiment, the method comprises detecting at least one mutation, such as 252C→G, 982C→T, or 1538_1553del in a gene encoding NAGPA or an isolated or purified fragment thereof in a test sample, comprising forming a complex with an isolated or purified nucleic acid molecule comprising the NAGPA gene or an isolated or purified fragment thereof, obtained from a human, wherein the presence of at least one mutation is indicative of stuttering or a predisposition to stuttering in a human.

In another embodiment, the invention provides an isolated or purified nucleic acid molecule comprising a portion of the nucleotide sequence encoding any of GNPTAB, GNPTG or NAGPA, wherein the isolated or purified nucleotide sequence portion contains the mutated nucleotide and about 30 continuous nucleotides in the 5 prime direction from the location of the identified mutation. The invention also provides, in an embodiment, an isolated or purified nucleic acid molecule comprising a portion of the nucleotide sequence encoding any of GNPTAB, GNPTG or NAGPA, wherein the isolated or purified nucleotide sequence portion contains the mutated nucleotide and about thirty continuous nucleotides in the 3 prime direction from the location of the identified mutation. The length of the nucleotide sequence can vary, and it is contemplated for purposes of the invention, that the length of the isolated or purified nucleotide sequence portion can be, for example, at least about 17 nucleotides in length, or at least about 20 nucleotides in length, or at least about 25 nucleotides in length.

In an embodiment, the invention provides an isolated or purified amino acid sequence or peptide comprising a portion of the amino acid sequence encoding any of GNPTAB, GNPTG or NAGPA, wherein the isolated or purified amino acid sequence portion contains the mutated amino acid and about 25 continuous amino acids in the amino terminal direction from the location of the identified mutation. The invention also provides, in an embodiment, an isolated or purified amino acid sequence or peptide comprising a portion of the amino acid sequence encoding any of GNPTAB, GNPTG or NAGPA, wherein the isolated or purified amino acid sequence portion contains the mutated amino acid and about 25 continuous amino acids in the carboxy terminal direction from the location of the identified mutation. The length of the isolated or purified amino acid peptide sequence can vary, and it is contemplated for purposes of the invention, that the length of the isolated or purified amino acid sequence portion can also be, for example, at least about 10 amino acids in length, or at least about 15 amino acids in length, or at least about 20 amino acids in length.

The at least one mutation can be detected by a variety of techniques known in the art, e.g., by sequencing the GNPTAB, GNPTG or NAGPA genes, and comparing the sequence to the wild-type sequence. Alternatively, the at least one mutation may be detected by Southern blot hybridization, a method well known in the art. Yet another alternative is by allele-specific PCR amplification of genomic DNA.

In addition to the above, the invention provides a method of determining the level of nucleic acid comprising the isolated or purified wild-type GNPTAB, GNPTG or NAGPA genes or isolated or purified fragments thereof, and/or isolated or purified mutant GNPTAB, GNPTG or NAGPA genes or isolated or purified fragments thereof in a test sample comprising a isolated or purified nucleic acid comprising any of the wild-type GNPTAB, GNPTG or NAGPA genes or isolated or purified fragments thereof and/or an isolated or purified mutant GNPTAB, GNPTG or NAGPA genes or isolated or purified fragments thereof obtained from a human. An embodiment of the method comprises assaying the test sample for the level of isolated or purified nucleic acid comprising any of the wild-type GNPTAB, GNPTG or NAGPA genes or isolated or purified fragments thereof and/or any of the mutant GNPTAB, GNPTG or NAGPA genes or isolated or purified fragments thereof, wherein a decrease in the level of isolated or purified nucleic acid comprising any of the wild-type GNPTAB, GNPTG or NAGPA genes or isolated or purified fragments thereof and/or an increase in the level of isolated or purified nucleic acid comprising any of the mutant GNPTAB, GNPTG or NAGPA genes or isolated or purified fragments thereof in the test sample as compared to a control sample is indicative of stuttering or a predisposition to stuttering in a human.

The level of any of the wild-type GNPTAB, GNPTG or NAGPA genes or fragments thereof and/or any of the mutant GNPTAB, GNPTG or NAGPA genes or fragments thereof in a test sample obtained from a human is defined herein as the quantity of isolated or purified nucleic acid comprising any of the wild-type GNPTAB, GNPTG or NAGPA genes or fragments thereof and/or the quantity of isolated or purified nucleic acid comprising any of the mutant GNPTAB, GNPTG or NAGPA genes or fragments thereof in the test sample. "Decreased" and "increased" levels of any of the wild-type GNPTAB, GNPTG or NAGPA genes or fragments thereof and/or any of the mutant GNPTAB, GNPTG or NAGPA genes or fragments thereof are determined by a comparison of the level of any of the wild-type and/or any of the mutant GNPTAB, GNPTG or NAGPA genes or fragments thereof present in a test sample obtained from a human to any suitable control test sample. Suitable control test samples include, for example, a test sample obtained from the same human at a different point in time and a test sample obtained from a different human.

Various assays known in the art can be used to measure the presence and/or level of isolated or purified nucleic acid (i.e., DNA or RNA) comprising a wild-type GNPTAB, GNPTG or NAGPA gene or fragments thereof and/or a mutant GNPTAB, GNPTG or NAGPA gene or fragments thereof present in a test sample obtained from a human. For example, assays including PCR and microarray analysis can be used to detect the presence and/or absence of any of the wild-type GNPTAB, GNPTG or NAGPA gene or fragments thereof and/or any of the mutant GNPTAB, GNPTG or NAGPA gene or fragments thereof, as described, for example, in U.S. Pat. Nos. 6,197, 506 and 6,040,138. Moreover, it is understood that the type of assay used depends on whether the isolated or purified nucleic acid of interest being assayed is DNA or RNA. Assays for determining the level of isolated or purified DNA comprising any of the wild-type GNPTAB, GNPTG or NAGPA gene or fragments thereof and/or any of the mutant GNPTAB, GNPTG or NAGPA gene or fragments thereof in a test sample are well known in the art, and include, for example, Southern hybridization (i.e., a Southern blot), in situ hybridization and microarray analysis. Assays for determining the level of RNA (e.g., mRNA) comprising any of the wild-type GNPTAB, GNPTG or NAGPA gene or fragments thereof and/or any of the mutant GNPTAB, GNPTG or NAGPA gene or fragments thereof in a test sample include, for example, Northern hybridization (i.e., a Northern blot), in situ hybridization and microarray analysis.

The isolated or purified antibody or antibodies which is/are used in the context of the present invention can, themselves, be linked to a detectable label. Such a detectable label allows for the presence of, or the amount of, the primary immune complexes to be determined. Alternatively, the first added component that becomes bound within the primary immune complexes can be detected by means of a second binding ligand that has binding affinity for the first antibody. In these cases, the second binding ligand is itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

The invention also provides for the use of the method in prognosticating stuttering in a human. In an embodiment, the method comprises comparing the level of any of the isolated or purified wild-type GNPTAB, GNPTG or NAGPA proteins or isolated or purified peptide fragments thereof, and/or any of the mutant GNPTAB, GNPTG or NAGPA proteins or isolated or purified peptide fragments thereof in the test sample, to the level of any of the isolated or purified wild-type GNPTAB, GNPTG or NAGPA proteins or isolated or purified peptide fragments thereof, and/or any of the mutant GNPTAB, GNPTG or NAGPA proteins or isolated or purified peptide fragments thereof, respectively, in another test sample obtained from a human over time, wherein a decrease in the level of any of the isolated or purified wild-type GNPTAB, GNPTG or NAGPA proteins or isolated or purified peptide fragments thereof, and/or an increase in the level of any of the mutant GNPTAB, GNPTG or NAGPA proteins or isolated or purified peptide fragments thereof is indicative of an unfavorable prognosis. Whereas an increase in the level of any of the wild-type GNPTAB, GNPTG or NAGPA proteins or isolated or purified peptide fragments thereof, and/or a decrease in the level of any of the mutant GNPTAB, GNPTG or NAGPA proteins or isolated or purified peptide fragments thereof, is indicative of a favorable prognosis, and no change in the level of any of the wild-type GNPTAB, GNPTG or NAGPA proteins or isolated or purified peptide fragments thereof, and/or any of the mutant GNPTAB, GNPTG or NAGPA proteins or isolated or purified peptide fragments thereof is indicative of no change in the stuttering.

The term "GNPTAB" as used herein refers to the enzyme N-acetylglucosamine-1-phosphotransferase (E.C. 2.7.8.17) α and β subunits. The enzyme is a complex of six polypeptides. The α- and β-subunits are the product of a single gene. Following translation, the α- and β-subunits are separated by proteolytic cleavage between Lys929 and Asp930. The α-subunit is a type II membrane glycoprotein with a single amino terminal membrane spanning domain. The β-subunit is a type I membrane spanning glycoprotein with a single carboxyl terminal membrane spanning domain. GNPTAB, in association with the γ subunit, catalyzes the transfer of N-acetylglucosamine-1-phosphate from UDP-GlcNAc to the 6 position of a 1,2-linked mannoses on the lysosomal enzyme. The recognition and addition of N-acetylgluocosamine-1-phosphate to lysosomal hydrolases by GNPTAB is the critical and determinive step in lysosomal targeting.

The term "GNPTG" as used herein refers to the regulatory γ subunit of the enzyme N-acetylglucosamine-1-phosphotransferase. The y-subunit is the product of a second gene. The γ-subunit is a soluble protein with a cleaved signal peptide. The α-, β-, and γ-subunits are all tightly associated.

The term "NAGPA" as used herein refers to the enzyme N-acetylglucosamine-1-phosphotransferase alpha-N-acetyl-glucosamidase (E.C. 3.1.4.45), which is capable of catalyzing the removal of N-acetylglucosamine from GlcNAc-phosphate-mannose diester-modified lysosomal enzymes to generate a terminal mannose-6-phosphate or "M6P". NAGPA is a tetramer composed of four identical subunits which are arranged as two non-covalently associated dimmers, which are themselves disulfide-linked. The single subunit is a type I membrane protein containing a signal peptide, a pro region not present in the mature enzyme, and a single carboxyl terminal membrane spanning domain.

The terms "GNPTAB/G" and "NAGPA" as used herein refer to isolated or purified enzymes obtained from any eukaryotic species, particularly mammalian species such as bovine, porcine, murine, equine, and human, and from any source whether natural, synthetic, semi-synthetic, or recombinant. The terms encompass isolated or purified membrane-bound enzymes and soluble or truncated enzymes having less than the complete amino acid sequence and biologically active variants and gene products.

The polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The isolated or purified polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the isolated or purified polypeptides and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The isolated or purified polypeptides, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 2007. Further, some of the polypeptides, and proteins of the invention (including functional portions and functional variants thereof) can be isolated and/or purified from a source, such as a plant, a bacterium, an insect, a mammal, e.g., a rat, a mouse, a human, etc. Methods of isolation and purification are well-known in the art. Alternatively, the polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, and proteins can be synthetic, recombinant, isolated, and/or purified.

Included in the scope of the invention are conjugates, e.g., bioconjugates, comprising any of the inventive polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg. Chem.* 44(15): 5405-5415 (2005)).

By "nucleic acid" as used herein includes "polynucleotide," "oligonucleotide," and "nucleic acid molecule," and generally means an isolated or purified polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex fowled upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The isolated or purified nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50° C.-70° C. Such high stringency conditions tolerate little, if any, mismatch between the nucleotide sequence and the template or target strand, and are particularly suitable for detecting expression of any of the GNPTAB, GNPTG or NAGPA proteins. It is generally appreciated that conditions can be rendered more stringent by the addition of increasing amounts of formamide.

The isolated or purified nucleic acids of the invention can be incorporated into a recombinant expression vector. In this regard, an embodiment of the invention provides recombinant expression vectors comprising any of the isolated or purified nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

In an embodiment, the present invention also provides for an expression vector comprising the isolated or purified nucleic acid molecule of any of SEQ ID NO: 1-4, 9-11 and 15-17 or isolated or purified sequences which are complementary thereto, in operative association with a nucleotide regulatory sequence that controls expression of the nucleic acid molecule in a host cell.

The recombinant expression vector can comprise a native or normative promoter operably linked to a nucleotide sequence encoding any of the mutated GNPTAB, GNPTG or NAGPA polypeptides or proteins (including functional portions and functional variants thereof), or to a nucleotide sequence which is complementary to or which hybridizes to a nucleotide sequence encoding any of the mutated GNPTAB, GNPTG or NAGPA, polypeptides or proteins. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant mutated GNPTAB, GNPTG or NAGPA polypeptide, or protein, the host cell is preferably a mammalian cell. Most preferably, the host cell is a human cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

Another embodiment of the invention further provides an antibody, or antigen binding portion thereof, which specifically binds to any of the GNPTAB, GNPTG or NAGPA proteins or isolated or purified peptide fragments thereof described herein. In one embodiment, the antibody, or antigen binding portion thereof, binds to an epitope or peptide fragment which contains any of the mutant amino acids which differ from the wild-type proteins. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the mutated portion of the GNPTAB, GNPTG or NAGPA proteins or peptide fragments thereof of the present invention, such that there is minimal cross-reaction with other peptides or proteins.

Methods of testing antibodies for the ability to bind to any functional portion of any of the inventive GNPTAB, GNPTG or NAGPA proteins or isolated or purified peptide fragments thereof are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 7$^{th}$ Ed., Garland Publishing, New York, N.Y. (2007)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The GNPTAB, GNPTG or NAGPA polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The invention also provides a method of treating a human prophylactically or therapeutically for stuttering, wherein the stuttering is due to a complete or partial loss of any of the wild-type GNPTAB, GNPTG or NAGPA genes or proteins expressed, the method comprises providing an isolated or purified non-mutant or wild-type form of GNPTAB, GNPTG or NAGPA protein to a human, whereupon a human is treated prophylactically or therapeutically for stuttering. Use of the terms "prophylactically," "prophylaxis," and derivatives of these terms is not meant to be limited to absolute prevention of stuttering, but also less than 100% prevention of stuttering. The ordinarily skilled artisan will appreciate that a less than 100% prevention of stuttering may still be beneficial to a human, and thus contemplated to be within the scope of the present invention.

In an embodiment the present invention provides a method for the treatment of stuttering or the predisposition for stuttering by administering a disease treating amount of the wild-type GNPTAB, GNPTG or NAGPA protein to a patient having one of the mutations identified herein. While dosages may vary depending on the disease and the patient, the protein is generally administered to the patient in amounts of from about 0.1 to about 1000 milligrams per 50 kg of patient per month, preferably from about 1 to about 500 milligrams per 50 kg of patient per month. Within the disease, the severity and the age at which stuttering presents may be a function of the amount of residual functioning protein that exists in the patient. As such, the present method of treating stuttering or the predisposition for stuttering in patients having one of the mutations identified herein includes providing the non-mutant wild-type GNPTAB, GNPTG or NAGPA proteins and a pharmaceutically acceptable carrier at any or all stages of stuttering.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular GNPTAB, GNPTG or NAGPA protein, as well as by the particular method used to administer the GNPTAB, GNPTG or NAGPA protein. Accordingly, there are a variety of suitable formulations of the pharmaceutical composition of the invention. The following formulations for parenteral, subcutaneous, intravenous, intramuscular, intraarterial, intrathecal, and interperitoneal administration are exemplary and are in no way limiting. More than one route can be used to administer the GNPTAB, GNPTG or NAGPA protein, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the GNPTAB, GNPTG or NAGPA proteins in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)). Preferably, when administering cells, e.g., dendritic cells, the cells are administered via injection.

For purposes of the invention, the amount or dose of the GNPTAB, GNPTG or NAGPA protein administered should be sufficient to effect, e.g., a therapeutic or prophylactic response, in the subject over a reasonable time frame. The dose will be determined by the efficacy of the particular GNPTAB, GNPTG or NAGPA protein and the condition of a human, as well as the body weight of a human to be treated.

The dose of the GNPTAB, GNPTG or NAGPA protein also will be determined by the existence, nature and extent of any adverse side effects that might accompany the administration of a particular GNPTAB, GNPTG or NAGPA protein. Typically, the attending physician will decide the dosage of the GNPTAB, GNPTG or NAGPA protein with which to treat each individual patient, taking into consideration a variety of factors, such as age, body weight, general health, diet, sex, GNPTAB, GNPTG or NAGPA protein to be administered, route of administration, and the severity of the condition being treated. By way of example and not intending to limit the invention, the dose of the GNPTAB, GNPTG or NAGPA protein can be about 0.001 to about 1000 mg/kg body weight of the subject being treated/day, from about 0.01 to about 10 mg/kg body weight/day, about 0.01 mg to about 1 mg/kg body weight/day.

Alternatively, the GNPTAB, GNPTG or NAGPA protein can be modified into a depot form, such that the manner in which the GNPTAB, GNPTG or NAGPA protein is released into the body to which it is administered is controlled with respect to time and location within the body (see, for example, U.S. Pat. No. 4,450,150). Depot forms of GNPTAB, GNPTG or NAGPA proteins can be, for example, an implantable composition comprising the GNPTAB, GNPTG or NAGPA proteins and a porous or non-porous material, such as a polymer, wherein the GNPTAB, GNPTG or NAGPA protein is encapsulated by or diffused throughout the material and/or degradation of the non-porous material. The depot is then implanted into the desired location within the body and the GNPTAB, GNPTG or NAGPA proteins are released from the implant at a predetermined rate.

Also provided is a method of detecting the presence of any of the mutant GNPTAB, GNPTG or NAGPA genes in a host. The method comprises (i) contacting a sample comprising any of the inventive isolated or purified GNPTAB, GNPTG or NAGPA polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of stuttering or the predisposition of stuttering in the host.

With respect to the inventive method of detecting any of the GNPTAB, GNPTG or NAGPA proteins or nucleic acid molecules in a host, the sample of cells of the host can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting step can take place in vitro or in vivo with respect to the host. Preferably, the contacting is in vitro.

Also, detection of the complex can occur through any number of ways known in the art. For instance, the inventive GNPTAB, GNPTG or NAGPA polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

EXAMPLES

The following examples further illustrate the invention but, of course, should not be construed as in any way limiting its scope.

Example 1

Applicants identified stuttering families in specialized populations to overcome a number of potential factors that have confounded earlier studies. One such population is Pakistan, where the majority of marriages are consanguineous (Hussain & Bittles, J. Biosocial Sci., 30:261-275 (1998)). Such inbred populations frequently reveal recessive and additive genetic mutations (Jaber et al., Community Genetics, 1:12-17 (1998)).

An analysis of this region of chromosome 12 was performed in detail in a group of Pakistani stuttering families and in a series of unrelated cases and controls from Pakistan and North America. Applicants surprisingly found for the first time, a genetic basis for stuttering in humans. The present invention discloses that mutations in three identified genes which comprise a single biochemical pathway in mammalian cells involved in targeting proteins for the lysozome in the cells of humans and most mammals, are involved in the etiology of stuttering in humans.

To identify the mutation associated with stuttering that resides in this region in Pakistani families, a genome-wide linkage study in a group of 41 consanguineous Pakistani families was initially performed and a strong linkage signal on chromosome 12q was identified. Comparative genomic hybridization (CGH) using microarrays was used to search for chromosomal abnormalities, such as insertions or deletions that could be responsible for stuttering. Applicants also performed a targeted population-based association study, in which they genotyped 503 single nucleotide polymorphisms (SNPs) across the 10 cM linkage region originally observed by Riaz et al. A comparison of allele frequencies in a group of 96 unrelated Pakistani stutterers and 96 normal Pakistani controls was then performed.

A systematic study of this 10 megabase genomic region (extending from the marker D12S101 at base pair 94,220,151 to the marker D12S1597 at base pair 104,175,626) in Pakistani stuttering families was performed using a variety of genome analysis methods, including (CGH) microarray analysis and DNA sequencing of coding and non-coding regions. Microarray CGH studies revealed no insertions, deletions, or copy number variants down to a resolution of 210 base pair in the seven affected Pakistani subjects.

After DNA sequencing of one contiguous 300 kb section of this interval along with the exons and exon-intron boundaries of 45 genes, the sequencing revealed numerous coding variants in stuttering (affected) individuals. Segregation of these variants was tested in family PKST72, a large Pakistani family showing strong genetic linkage on chromosome 12. Because these genes all reside within the region of linkage, most of these variants segregated to some degree with stuttering in this family. However, most of these variants were found at high frequency (>5%) in the normal Pakistani population, and thus represent likely nonpathogenic polymorphisms.

Applicants then obtained DNA and speech samples from 24 additional members of kindred PKST72, the largest family in the sample. Subsequent genotyping and linkage analysis confirmed a strong linkage on chromosome 12q, but the location of the strongest evidence for linkage shifted slightly, approximately 1.6 centimorgans in the proximal direction. A systematic evaluation of all identifiable genes within the entire region showing linkage (87 genes) was then initiated, using DNA sequencing of all exons and exon/intron boundaries. Overall, an evaluation of a total of 45 genes within the linkage region was undertaken. One gene, residing closest to the new linkage peak, was found to have an apparent mutation that segregated with affected individuals in family PKST72. This gene was identified as GNPTAB.

The variant or mutation showing the highest degree of co-segregation with stuttering in PKST72 was a G3598A codon substitution that results in a lysine in place of the normal glutamic acid at amino acid position 1200 in the GNPTAB protein (reference mRNA sequence NM_24312). In the PKST72 family, all affected individuals carried either one or two copies of this variant, with two exceptions. These exceptions were two female family members who each carried one copy of the lysine variant, but were reported to be unaffected. In addition, three affected individuals were homozygous for the normal glutamic acid allele at this position. Further inspection of the genotypes of these three individuals revealed that they carried a different haplotype of the GNPTAB region than all other affected members of the family, supporting the hypothesis that these three individuals stutter due to a genetic variant other than the glu1200lys mutation in the GNPTAB gene.

The glu1200lys mutation was also observed in affected individuals in three other Pakistani stuttering families (PKST5, PKST25, and PKST41), and thus its occurrence in 4 out of a total of 41 families in our sample suggests this mutation is present in approximately 10% of Pakistani stuttering families. This mutation was also observed homozygous in one affected American individual of Asian Indian ancestry, suggesting this mutation is most common in populations from the Asian sub-continent. Subsequent DNA sequencing revealed three other mutations in the GNPTAB gene in four unrelated affected individuals, as summarized in Table 1.

TABLE 1

Summary of mutations identified in GNPTAB gene in stutterers

| Mutation number | GNPTAB exon | Base pair change | Amino acid change | Subject |
|---|---|---|---|---|
| 1 | 19 | G > A | Glu 1200 Lys | many |
| 2 | 9 | A > G | Ser 321 Gly | PKSTR 59 |
| 3 | 11 | G > T | Ala 455 Ser | NA 56, 264 |
| 4 | 13 | C > G | Phe 624 Leu | PKSTR 51 |

The glu1200lys mutation was not found in the samples of 192 chromosomes from normal Pakistani controls, or in the samples of 540 chromosomes from neurologically normal North American controls. Comparative analysis revealed that the normal amino acid at each of these 4 positions in the GNPTAB protein is conserved in other mammals, further supporting the view that these variants represent pathological mutations.

In addition to the glu1200lys mutation in GNPTAB, nine additional variants were identified in other genes within the linkage interval that was associated with stuttering at more than a random level in family PKST72. All of these variants occur at high frequency (0.14-0.50) in the normal Pakistani population, indicating they are non-pathogenic.

The glu1200lys mutation was then searched in the DNA collected from a large group of unrelated stutterers, all of whom have a family history of stuttering, and are thus likely to stutter due to a genetic cause. Five chromosomes were identified carrying this mutation in a sample of 96 unrelated Pakistani stutterers, while only one of 192 chromosomes from normal Pakistani population showed this same variant. Two copies of the lysine variant were also identified in an individual of Indian descent, in our sample of 272 unrelated stutterers (designated the NA sample) from the United States. The GNPTAB gene was then sequenced from the DNA from samples of 276 documented neurologically normal individuals. All of these 552 normal chromosomes carried the normal glutamic acid at this position.

Further study was then undertaken to determine whether other mutations in GNPTAB occur in people who stutter. Subsequent sequencing of all 21 exons of GNPTAB in DNA samples from 395 unrelated stutterers located in the U.S. and Pakistan revealed 17 novel variants not listed in the current SNP database. Some of these variants identified also occurred in normal controls, or they resulted in changed amino acids that are not well conserved in the GNPTAB protein, suggesting that these variants are rare normal polymorphisms of the GNPTAB gene, and not pathogenic.

Three GNPTAB variants were found in affected individuals that did not occur in samples of 552 chromosomes from neurologically normal (non-stuttering) controls (mutations 2, 3 and 4, Table 1). All three of these mutations changed amino acids that are highly conserved. Mutations 2 and 4 were found in two Pakistani individuals. Mutation 3 was found in two European individuals. These data indicate that other, relatively rare mutations in the GNPTAB gene can cause stuttering in other dissimilar populations, such as Europeans.

Example 2

The GNPTG gene (mRNA reference sequence NM_032520), which encodes the regulatory subunit of GNPTAB was evaluated next. Three mutations were identified in four unrelated affected individuals (Table 2). None of these mutations were present in the samples of 192 chromosomes from normal Pakistani controls or in the samples of 540 chromosomes from neurologically normal North American controls as well. A missense mutation was observed at amino acid position 74 of GNPTG encodes a negatively charged glutamic acid in place of the small non-polar amino acids (alanine or glycine) at this position. A second mutation was found at position 688 of GNPTG encodes a valine in place of leucine at this position. The third mutation identified was a nine base pair duplication, encoding an in-frame duplication of amino acids 5, 6, and 7 of GNPTG.

Example 3

The GNPTAB/G enzyme acts in a pathway that generates the mannose-6 phosphate targeting signal that directs enzymes to the lysozome. The subsequent step in this pathway is catalyzed by N-acetylglucosamine-1-phosphodiester alpha-N-acetylglucosaminidase (NAGPA) (mRNA reference sequence NM_016256), also known as the uncovering enzyme. DNA sequencing of 6 unrelated affected individuals revealed three different mutations in NAGPA (Table 2). None of these mutations were present in samples from the 192 normal Pakistani and 540 normal North American control chromosomes. The first mutation identified was located at position 328 of NAGPA, and encodes a cysteine in place of an arginine at that position. The second mutation was found at position 84 of NAGPA, and encodes a glutamine in place of the normal histidine that is found in humans. The third mutation identified was a 16 base pair deletion, which changes the penultimate amino acid from lysine to asparagine, and removes the last amino acid and the stop codon from the reading frame. As a result of this mutation, an extended open reading frame is created that provides the addition of 113 extra amino acids to the carboxy terminus of this protein (FIG. 1).

263 unrelated cases from the United States and 25 from England (collectively referred to as our North American sample) were enrolled by public appeal, using the following screening criteria: age 8 years and over, stuttering duration of 6 months or more, evidence of a family history of stuttering, speech characterized more than 4% stuttering dysfluencies, measured using the Stuttering Severity Instrument, $3^{rd}$ edition (SSI-3, Riley, G. Stuttering Severity Instrument for Children and Adults (3 ed.). Western Psychological Services, Los Angeles. 1980) or a well characterized standard reading passage (Webster, Empirical considerations regarding stuttering. Chapter 6, in Controversies about stuttering therapy. Gregory H, ed. University Park Press, Baltimore 1978) available from the author, and no other self-reported neurologic or psychiatric symptoms. Pakistani controls consisted of age and gender matched individuals with normal speech from the same region of Pakistan. All subjects were enrolled with written informed consent approved by Institutional Review Boards of the National Institutes of Health and the University of Punjab, Lahore (NIH/NINDS #97-DC-0057). North American con-

TABLE 2

Mutations found in GNPTAB, GNPTG and NAGPA genes.

| | Mutation | Amino acid change | Pakistani stutterers (N = 123) | Pakistani controls (N = 97) | North American stutterers (N = 270) | North American controls (N = 276) | Mutant genotype: subject number, (ancestry) |
|---|---|---|---|---|---|---|---|
| GNPTAB | | | | | | | |
| Exon9 | c.961A > G | p.Ser321Gly | 1 | 0 | 0 | 0 | A/g: PKSTR59 (SA) |
| Exon11 | c.1363G > T | p.Ala455Ser | 0 | 0 | 2 | 0 | G/t: NA56 (E), NA264 (E) |
| Exon13 | c.1875C > G | p.Phe624Leu | 1 | 0 | 0 | 0 | C/g: PKSTR51 (SA) |
| Exon19 | c.3598G > A | p.Glu1200Lys | 9 | 1 | 0 | 0 | NA43(SA), PKST25 (SA), PKST5 (SA), PKST72 (SA), PKST41 (SA), PKSTR69 (SA), PKSTR74 (SA), RNP62 (SA) |
| GNPTG | | | | | | | |
| Exon1 | c.11_19dup | p.Leu5_Arg7dup | 0 | 0 | 1 | 0 | NA21 (E) |
| Exon2 | c.74C > A | p.Ala25Glu | 0 | 0 | 2 | 0 | C/g: NA66 (E), NA273 (E) |
| Exon9 | c.688C > G | p.Leu230Val | 0 | 0 | 1 | 0 | C/g: NA247 (SA) |
| NAGPA | | | | | | | |
| Exon2 | c.252C > G | p.His84Glu | 0 | 0 | 2 | 0 | C/g: NA20 (E), NA207 (E) |
| Exon6 | c.982C > T | p.Arg328Cys | 0 | 0 | 4 | 0 | t/t: NA288 (E) C/t: NA177 (E), NA195 (E) |
| Exon10 | c.1538_1553del | p.Phe513SerfsX113 | 0 | 0 | 1 | 0 | Del16bp NA229 (E) |

Subject numbers:
PKSTR = unrelated Pakistani affected,
NA = unrelated North American affected,
PKST = Pakistani stuttering family,
RNP = unrelated normal Pakistani.
Ancestry:
SA = South Asian,
E = European.
Reference sequences for numbering the mutation positions in GNPTAB, GNPTG and NAGPA are NM_024312, NM_032520 and NM_016256 respectively.

Pakistani families were enrolled as described in Riaz et al. Ninety-six unrelated stuttering cases from Pakistan, as well as trols consisted of 288 well-characterized neurologically normal Caucasians (DNA Panels NDTP006, NDPT020, and NDPT023, Coriell Institute, Camden, N.J.). Gene identification and bioinformatic analyses were based on the UCSC Genome Browser, March 2006 assembly (http://genome.ucsc.edu/cgi-bin/hgTracks). Comparative genomic hybridization (Pinkel et al.) was performed using a custom CGH 385KArray (Nimblegen, Inc.) designed to query 10 Mb centered on base pair 100,000,000 of the chromosome 12 sequence in 7 affected and 3 normal Pakistani individuals. DNA sequencing was performed on genomic DNA purified from blood using standard methods. Protein sequence alignments were performed using MultAlin 5.4.1 (Corpet, http://www-archbac.u-psud.fr/genomics/multalin.html).

Example 4

In order to identify the polymorphisms of interest in each of the three genes, each of the exons for GNPTAB, GNPTG and NAGPA were isolated and sequenced in the each of the subjects in the study and compared to known wild-type controls. Unique DNA primers for the exons for GNPTAB, GNPTG and NAGPA were then constructed from this information using techniques known in the art and discussed below. Mouse and human blood samples were taken and mRNA transcripts were purified from the extracted samples. Methods of cell lysis and subsequent mRNA purification are well-known in the art. These primers are employed in reverse transcriptase-polymerase chain reaction RT-PCR) and 5'- and 3'-rapid amplification of cDNA ends (RACE) on the purified mRNA from blood samples and used to identify the polymorphisms in the genes.

PCR Reactions

The oligonucleotides (FIGS. 11A-11D) for PCR amplification and sequencing were designed by Primer 3 software (http://www-genome.wi.mit.edu/cgi-bin/primer/primer3_www.cgi). PCR reactions to amplify most exons were performed (Table 3A) on 20 ng of genomic DNA template in a volume of 10 µl, and each reaction contained 0.2 µM of forward and reverse primers; 0.2 units of HotStar Taq® polymerase (Qiagen, Valencia, Calif. 91355); 1 mM of $MgCl_2$; 200 µM of dNTP with the same amount of dATP, dCTP, dTTP, dGTP. PCR amplifications were performed in 96-well plates. The Failsafe™ PCR system (Table 3B) with buffer G was used to amplify exon1 in GNPTAB, exons 1, 2, and 3 in GNPTG, and exons 1 and 2 in NAGPA. All other exons were amplified using Qiagen's HotStar Taq® as described above.

The thermocycling parameters for the PCR amplification consisted of an initial denaturation cycle at 95° C. for 15 minutes, followed by 35 cycles at 94° C. for 20 seconds, 56° C. for 30 seconds, and 72° C. for 1 minute, and a final extension step at 72° C. for 7 minutes by using the GeneAmp PCR system 9700 (Applied Biosystems, Foster City, Calif. 94404).

After PCR reaction, the non-incorporated dNTPs and remaining unincorporated primers were removed by adding 0.114 unit of shrimp alkaline phosphatase and 0.24 unit of exo I to each PCR product, and then thermocycling, comprising an initial incubation step at 37° C. for 30 minutes, followed by inactivation step at 80° C. for 10 minutes. Thermocycled DNA products treated with shrimp alkaline phosphatase were used as a template for the subsequent BigDye® sequencing reaction step.

Big-Dye® Reactions

All primer extension reactions (Table 6) were performed in a total reaction volume of 10 µl and each reaction contained 0.16 µM of sequencing primer; 0.3 µl of BigDye® Terminator v3.1 mix; and 1× sequencing buffer. The thermocycling parameters (Table 5) for the primer extension consisted of an initial denaturation cycle at 96° C. for 1 min followed by 25 cycles at 96° C. for 10 sec, 50° C. for 5 sec, and 60° C. for 3 min. After primer extension, reaction products were partially purified by ethanol precipitation and analyzed by electrophoresis using an ABI capillary sequencing instrument.

TABLE 3A

PCR reaction mixture for Qiagen HotStar Taq ®

| Reagent | Final Conc. | Vol. (µl) for 10 µl reaction |
|---|---|---|
| DDW | NA | 5.36 |
| 10 X PCR buffer | 1 X | 1 |
| $MgCl_2$ (25 mM) | 2.5 mM | 0.4 |
| dNTP (10 mM) | 200 uM each | 0.2 |
| Primer mix (2 uM) each) | 0.2 uM each | 1 |
| Hotstar Taq ® (5 U/ul) | 0.025 U/ul | 0.04 |
| Genomic DNA ® (10 ng/ul) | 2 ng/ul | 2 |
| Total vol | | 10 |

TABLE 3B

PCR reaction mixture for Epicentre Failsafe ™
PCR system (Cat No: FSE51100 (Taq), FSP995G (Buffer)(Epicentre Biotechnologies, Madison, WI)

| Reagent | Final Conc. | Vol. (µl) for 10 ul reaction |
|---|---|---|
| DDW | NA | 5.8 |
| 10 X PCR buffer mix, G | 1 X | 1 |
| Primer mix (2 uM) each) | 0.2 µM each | 1 |
| Failsafe Taq (2.5 U/ul) | 0.5 U/µl | 0.2 |
| Genomic DNA (10 ng/ul) | 2 ng/µl | 2 |
| Total vol. | | 10 |

TABLE 4

Thermocycling PCR Reaction Conditions

| | Time | Temperature |
|---|---|---|
| 1. Initial activation step | 15 min | 95° C. |
| 2. Cycling (35 Cycles) | | |
| Denaturation | 20 sec | 94° C. |
| Annealing | 30 sec | 56° C. |
| Extension | 1 min | 72° C. |
| 3. Final extension | 10 min | 72° C. |
| | ∞ | 4° C. |

TABLE 5

PCR Clean-up Reaction Mixture

| Reagent | Final Conc. | Vol. (µl) for 10 µl PCR |
|---|---|---|
| DDW | | 7.862 |
| SAP buffer (10X) | 1X | 2 |
| SAP (1 U/µl) | | 0.114 |
| Exo I (10 U/µl) | | 0.024 |
| Total Vol. | | 10 |

For the PCR clean up process, 10 μl of SAP/ExoI sol was added to the 10 μl of PCR Product and incubated at 37° C. for 30 minutes, followed by a second incubation at 80° C. for 10 minutes.

TABLE 6

BigDye ® PCR Reaction Mixture

| Reagent | Final Conc. | Vol. (μl) for 10 ul reaction |
|---|---|---|
| DDW | | 4.8 |
| Sequencing Buffer | 1 X | 2 |
| Primer (1.6 uM) | 0.16 μM | 1 |
| BigDye ® Master mix | 1/6.7 X | 0.3 |
| Template (After PCR clean-up) | | 2 |
| | Total Vol. | 10 |

TABLE 5

Thermocycling conditions for BigDye ® Reaction

| | Time | Temperature |
|---|---|---|
| 1. Initial activation step | 1 min | 96° C. |
| 2. Cycling (25 Cycles) | | |
| Denaturation | 10 sec | 96° C. |
| Annealing | 5 sec | 50° C. |
| Extension | 3 min | 60° C. |
| | ∞ | 4° C. |

The resulting cDNA molecules that were generated were then sequenced and identified as either wild-type or mutant forms of GNPTAB, GNPTG or NAGPA when compared to the sequences identified in the present invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of screening human patients to identify those patients having a genetic mutation indicative of stuttering or a predisposition to stuttering comprising:
   (a) obtaining a sample of genetic material from the patients,
   (b) assaying the sample for the presence of a genotype in the patients which is indicative of stuttering or a predisposition to stuttering, and
   (c) identifying those patients that stutter or are more likely to exhibit a predisposition to stuttering by correlating the presence of a genotype in the patients which is associated with stuttering in (b), with the identity of the patients which provided the sample;
   wherein the genotype includes a mutation in a gene of N-acetylglucosamine-1-phosphodiester alpha-N-acetylglucosaminidase (NAGPA) and wherein the mutated forms are selected from the group consisting of: the allelic variant at position 252 where a C is substituted by a G codon (SEQ ID NO: 15); the allelic variant at position 982 where a C is substituted by a T codon (SEQ ID NO: 16); and the allelic variant at position 1538 where there is a 16 base pair deletion (SEQ ID NO: 17).

2. The method of claim 1, wherein assaying for the presence of the genotype comprises detecting the presence of at least one or more of the following polynucleotide sequences SEQ ID NO: 15, SEQ ID NO: 16, SEQ ID NO: 17, or combinations thereof.

* * * * *

SEQUENCE LISTING

```
<160> NUMBER OF SEQ ID NOS: 236

<210> SEQ ID NO 1
<211> LENGTH: 40
<212> TYPE: DNA
<213> ORGANISM: Homo sapiens

<400> SEQUENCE: 1
aggatgaaga catctctgcc ggtcgttttg aagataacga                      40

<210> SEQ ID NO 2
<211> LENGTH: 40
<212> TYPE: DNA
<213> ORGANISM: Homo sapiens

<400> SEQUENCE: 2
aggatggcta ttgtgacaag tcttgtaata attcagcctg                      40

<210> SEQ ID NO 3
<211> LENGTH: 40
<212> TYPE: DNA
<213> ORGANISM: Homo sapiens

<400> SEQUENCE: 3
```
aatacaaacg atgaagagtt gaaaatgcag ataacagtgg                                40

<210> SEQ ID NO 4
<211> LENGTH: 40
<212> TYPE: DNA
<213> ORGANISM: Homo sapiens

<400> SEQUENCE: 4
ttcatatgca tgagctgcag aaatggaggg cttatcgaga                                40

<210> SEQ ID NO 5
<211> LENGTH: 20
<212> TYPE: PRT
<213> ORGANISM: Homo sapiens

<400> SEQUENCE: 5

Gln Ser Lys Gln Asp Glu Asp Ile Ser Ala Gly Arg Phe Glu Asp Asn
1               5                   10                  15

Glu Glu Leu Arg
            20

<210> SEQ ID NO 6
<211> LENGTH: 20
<212> TYPE: PRT
<213> ORGANISM: Homo sapiens

<400> SEQUENCE: 6

Ser Trp Ile Lys Asp Gly Tyr Cys Asp Lys Ser Cys Asn Asn Ser Ala
1               5                   10                  15

Cys Asp Trp Asp
            20

<210> SEQ ID NO 7
<211> LENGTH: 20
<212> TYPE: PRT
<213> ORGANISM: Homo sapiens

<400> SEQUENCE: 7

Leu Thr Phe Gln Asn Thr Asn Asp Glu Glu Leu Lys Met Gln Ile Thr
1               5                   10                  15

Val Glu Val Asp
            20

<210> SEQ ID NO 8
<211> LENGTH: 20
<212> TYPE: PRT
<213> ORGANISM: Homo sapiens

<400> SEQUENCE: 8

Asn Arg Phe Leu His Met His Glu Leu Gln Lys Trp Arg Ala Tyr Arg
1               5                   10                  15

Asp Lys Leu Lys
            20

<210> SEQ ID NO 9
<211> LENGTH: 49
<212> TYPE: DNA
<213> ORGANISM: Homo sapiens

<400> SEQUENCE: 9
ggcgcgatgg cggcggggct ggcgcggctg gcgcggctcc tgttgctcc                      49

-continued

<210> SEQ ID NO 10
<211> LENGTH: 40
<212> TYPE: DNA
<213> ORGANISM: Homo sapiens

<400> SEQUENCE: 10
gcccgcgccg gcaggtgcag agaagatgaa ggtggtggag                              40

<210> SEQ ID NO 11
<211> LENGTH: 40
<212> TYPE: DNA
<213> ORGANISM: Homo sapiens

<400> SEQUENCE: 11
aagaaaatga acccacccag gtggagggag gtcctgacag                              40

<210> SEQ ID NO 12
<211> LENGTH: 37
<212> TYPE: PRT
<213> ORGANISM: Homo sapiens

<400> SEQUENCE: 12

Met Ala Ala Gly Leu Ala Arg Leu Ala Arg Leu Leu Leu Leu Leu Gly
1               5                   10                  15

Leu Ser Ala Gly Gly Pro Ala Pro Ala Gly Ala Ala Lys Met Lys Val
            20                  25                  30

Val Glu Glu Pro Asn
        35

<210> SEQ ID NO 13
<211> LENGTH: 34
<212> TYPE: PRT
<213> ORGANISM: Homo sapiens

<400> SEQUENCE: 13

Met Ala Ala Gly Leu Ala Arg Leu Leu Leu Leu Gly Leu Ser Ala
1               5                   10                  15

Gly Gly Pro Ala Pro Ala Gly Ala Glu Lys Met Lys Val Val Glu Glu
            20                  25                  30

Pro Asn

<210> SEQ ID NO 14
<211> LENGTH: 20
<212> TYPE: PRT
<213> ORGANISM: Homo sapiens

<400> SEQUENCE: 14

Lys Thr Pro Glu Glu Asn Glu Pro Thr Gln Val Glu Gly Gly Pro Asp
1               5                   10                  15

Ser Leu Gly Phe
            20

<210> SEQ ID NO 15
<211> LENGTH: 40
<212> TYPE: DNA
<213> ORGANISM: Homo sapiens

<400> SEQUENCE: 15
gtgcgcacct tcgtgtcgca gttcagggac cgcgcggtgg                              40

<210> SEQ ID NO 16
<211> LENGTH: 40
<212> TYPE: DNA

-continued

<213> ORGANISM: Homo sapiens

<400> SEQUENCE: 16
tggtgtgtgt gcacgaaccc tgctgccagc cgcctgactg        40

<210> SEQ ID NO 17
<211> LENGTH: 38
<212> TYPE: DNA
<213> ORGANISM: Homo sapiens

<400> SEQUENCE: 17
cccacaaccc ctcaagctgc ccggggtggc acgtcgcg         38

<210> SEQ ID NO 18
<211> LENGTH: 20
<212> TYPE: PRT
<213> ORGANISM: Homo sapiens

<400> SEQUENCE: 18

Gly Gly Leu Ala Val Arg Thr Phe Val Ser Gln Phe Arg Asp Arg Ala
1               5                   10                  15

Val Ala Gly His
            20

<210> SEQ ID NO 19
<211> LENGTH: 20
<212> TYPE: PRT
<213> ORGANISM: Homo sapiens

<400> SEQUENCE: 19

Val Ser Thr Val Val Cys Val His Glu Pro Cys Cys Gln Pro Pro Asp
1               5                   10                  15

Cys His Gly His
            20

<210> SEQ ID NO 20
<211> LENGTH: 25
<212> TYPE: PRT
<213> ORGANISM: Homo sapiens

<400> SEQUENCE: 20

Gly Glu Pro Leu Ala Ala Glu Lys Glu Gln Pro Gly Gly Ala His Asn
1               5                   10                  15

Pro Ser Ser Cys Pro Gly Trp His Val
            20                  25

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
ctgggctccc agactcct         18

<210> SEQ ID NO 22
<211> LENGTH: 22
<212> TYPE: DNA
<213> ORGANISM: Artificial Sequence
<220> FEATURE:
<223> OTHER INFORMATION: Synthetic

<400> SEQUENCE: 22

```
agttctgagg tcttttcaag ca                                            22

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tcctgttgag tggcagatgt                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
atcctttcct tggtgcctct                                               20

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
aatgctttga atgatggcaa c                                             21

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
tcgagactgt gccatagacg                                               20

<210> SEQ ID NO 27
<211> LENGTH: 26
<212> TYPE: DNA
<213> ORGANISM: Artificial Sequence
<220> FEATURE:
<223> OTHER INFORMATION: Synthetic

<400> SEQUENCE: 27
caccttccct atgcccctcc gtcctc                                        26

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
caggagcttg aacagcatca                                               20

<210> SEQ ID NO 29
<211> LENGTH: 18
<212> TYPE: DNA
<213> ORGANISM: Artificial Sequence
<220> FEATURE:
```

<223> OTHER INFORMATION: Synthetic

<400> SEQUENCE: 29
ctatgcccct ccgtcctc                                                 18

<210> SEQ ID NO 30
<211> LENGTH: 28
<212> TYPE: DNA
<213> ORGANISM: Artificial Sequence
<220> FEATURE:
<223> OTHER INFORMATION: Synthetic

<400> SEQUENCE: 30
aatcacatac atgccttttt ccagttct                                      28

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31
ttcacctgga tctaacacga tg                                            22

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tcagatgggc atactcctga                                               20

<210> SEQ ID NO 33
<211> LENGTH: 24
<212> TYPE: DNA
<213> ORGANISM: Artificial Sequence
<220> FEATURE:
<223> OTHER INFORMATION: Synthetic

<400> SEQUENCE: 33
tgtcatggtt ggattacttc ttca                                          24

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
tcagttttac cagatccttt tgt                                           23

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
cagcctggta ccatgtttta ct                                            22

<210> SEQ ID NO 36

```
<211> LENGTH: 23
<212> TYPE: DNA
<213> ORGANISM: Artificial Sequence
<220> FEATURE:
<223> OTHER INFORMATION: Synthetic

<400> SEQUENCE: 36
tgtacctaat ttggggtcaa aaa                                              23

<210> SEQ ID NO 37
<211> LENGTH: 25
<212> TYPE: DNA
<213> ORGANISM: Artificial Sequence
<220> FEATURE:
<223> OTHER INFORMATION: Synthetic

<400> SEQUENCE: 37
tccatgagat aaaagtcttc atttg                                            25

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
tgttttgctt ctctttgtgc at                                               22

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
ttttgtctcc ttcagcttcc tt                                               22

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
gcatcacaac acaagcttca a                                                21

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
gctgtttttc tttgagaatc ttttt                                            25

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
```
tggcagaaca gaatccctct                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
tgaggtgagc agagatcgtg                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
taccaaacca atggcagtga                                              20

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
tgctgtctct ttgaattttg g                                            21

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
aggaagggaa ggcaatgaag                                              20

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
ccctttaccc ttctacctcc a                                            21

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
tatgcttccc aagctggtct                                              20

<210> SEQ ID NO 49
<211> LENGTH: 20
<212> TYPE: DNA
<213> ORGANISM: Artificial Sequence
<220> FEATURE:

<223> OTHER INFORMATION: Synthetic

<400> SEQUENCE: 49
tcaacgcagc aggatctaaa 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
aggtttgcac caccacactt 20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
aggtgatcca gcctcctctg 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gaatgcaagg ctggtaaagg 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
caaggacgac atgcaaattc 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gcgtcttttg gaaggagtga 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
tacagcccag aagggttacg 20

<210> SEQ ID NO 56

```
<211> LENGTH: 20
<212> TYPE: DNA
<213> ORGANISM: Artificial Sequence
<220> FEATURE:
<223> OTHER INFORMATION: Synthetic

<400> SEQUENCE: 56
aatcagagat gggggctttt                                              20

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
tgcagaggtt gactttcct g                                             21

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
tcacacttgg gctgtttcct                                              20

<210> SEQ ID NO 59
<211> LENGTH: 22
<212> TYPE: DNA
<213> ORGANISM: Artificial Sequence
<220> FEATURE:
<223> OTHER INFORMATION: Synthetic

<400> SEQUENCE: 59
tttgctccta atgaagagtt cg                                           22

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
cttcagggaa cctgtccaaa                                              20

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
cgtgtttgag ttgtttgctt g                                            21

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
```

```
gctcagctgc ctcagcat                                                   18

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
tgggtatctc agaggccaga                                                 20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
aacaggacat ccgcttatgg                                                 20

<210> SEQ ID NO 65
<211> LENGTH: 23
<212> TYPE: DNA
<213> ORGANISM: Artificial Sequence
<220> FEATURE:
<223> OTHER INFORMATION: Synthetic

<400> SEQUENCE: 65
ttggtgtttt tcttacctcc aga                                             23

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
ccgtagtgga ctcaacatcc a                                               21

<210> SEQ ID NO 67
<211> LENGTH: 26
<212> TYPE: DNA
<213> ORGANISM: Artificial Sequence
<220> FEATURE:
<223> OTHER INFORMATION: Synthetic

<400> SEQUENCE: 67
taaaatttat atgagattgt ttgctg                                          26

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
actcaaccac cagctccaac                                                 20

<210> SEQ ID NO 69
<211> LENGTH: 20
<212> TYPE: DNA
<213> ORGANISM: Artificial Sequence
<220> FEATURE:
```

<223> OTHER INFORMATION: Synthetic

<400> SEQUENCE: 69
tcattccccc agagaatcat                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
agcttgggca acaagaacaa                                               20

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
ttgcaagaca atgtttttgt g                                             21

<210> SEQ ID NO 72
<211> LENGTH: 21
<212> TYPE: DNA
<213> ORGANISM: Artificial Sequence
<220> FEATURE:
<223> OTHER INFORMATION: Synthetic

<400> SEQUENCE: 72
ttgctgcctg aatattgtga a                                             21

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73
tggaagagga atgatggaga tt                                            22

<210> SEQ ID NO 74
<211> LENGTH: 21
<212> TYPE: DNA
<213> ORGANISM: Artificial Sequence
<220> FEATURE:
<223> OTHER INFORMATION: Synthetic

<400> SEQUENCE: 74
ggagcctctt agcaatcact c                                             21

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
gctcatggac ctgtcatcct                                               20

<210> SEQ ID NO 76

```
<211> LENGTH: 21
<212> TYPE: DNA
<213> ORGANISM: Artificial Sequence
<220> FEATURE:
<223> OTHER INFORMATION: Synthetic

<400> SEQUENCE: 76
cagtgccatc agcactactc a                                             21

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
gacttcagcc cctaagaatg c                                             21

<210> SEQ ID NO 78
<211> LENGTH: 21
<212> TYPE: DNA
<213> ORGANISM: Artificial Sequence
<220> FEATURE:
<223> OTHER INFORMATION: Synthetic

<400> SEQUENCE: 78
aggctgagac agaactgctt g                                             21

<210> SEQ ID NO 79
<211> LENGTH: 19
<212> TYPE: DNA
<213> ORGANISM: Artificial Sequence
<220> FEATURE:
<223> OTHER INFORMATION: Synthetic

<400> SEQUENCE: 79
gaccctcagg ccatcattt                                                19

<210> SEQ ID NO 80
<211> LENGTH: 22
<212> TYPE: DNA
<213> ORGANISM: Artificial Sequence
<220> FEATURE:
<223> OTHER INFORMATION: Synthetic

<400> SEQUENCE: 80
tcagcacaga acctgataca ca                                            22

<210> SEQ ID NO 81
<211> LENGTH: 19
<212> TYPE: DNA
<213> ORGANISM: Artificial Sequence
<220> FEATURE:
<223> OTHER INFORMATION: Synthetic

<400> SEQUENCE: 81
tcaccgatct cctcctcct                                                19

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
```
tgcccagaga atcctcctta                                             20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
ttgctgcgaa acaaacattc                                             20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
gagacaccgt ttgggaagat                                             20

<210> SEQ ID NO 85
<211> LENGTH: 19
<212> TYPE: DNA
<213> ORGANISM: Artificial Sequence
<220> FEATURE:
<223> OTHER INFORMATION: Synthetic

<400> SEQUENCE: 85
ccatagttca cggggttgg                                              19

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
cccgaggtcg tcttcattt                                              19

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gcaacggagg caaactagac                                             20

<210> SEQ ID NO 88
<211> LENGTH: 18
<212> TYPE: DNA
<213> ORGANISM: Artificial Sequence
<220> FEATURE:
<223> OTHER INFORMATION: Synthetic

<400> SEQUENCE: 88
gagagcgggt cagggttt                                               18

<210> SEQ ID NO 89
<211> LENGTH: 18
<212> TYPE: DNA
<213> ORGANISM: Artificial Sequence
<220> FEATURE:

-continued

<223> OTHER INFORMATION: Synthetic

<400> SEQUENCE: 89
aggccctcaa accctgac                                                 18

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
tcctccacca ccttcatctt                                               20

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
gttgctcctc gggctctc                                                 18

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
aaggctgaca aaccaatgct                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
aagatgaagg tggtggagga                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
acctctcgga aaggaaagga                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
cagactctgc cagtctttgc                                               20

<210> SEQ ID NO 96

-continued

```
<211> LENGTH: 18
<212> TYPE: DNA
<213> ORGANISM: Artificial Sequence
<220> FEATURE:
<223> OTHER INFORMATION: Synthetic

<400> SEQUENCE: 96
ctcccactcg tgccagat                                                 18

<210> SEQ ID NO 97
<211> LENGTH: 19
<212> TYPE: DNA
<213> ORGANISM: Artificial Sequence
<220> FEATURE:
<223> OTHER INFORMATION: Synthetic

<400> SEQUENCE: 97
gtgggatcct cgggtgagt                                                19

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
caagagaagc caggctcag                                                19

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
agctgagcct ggcttctctt                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
gccagcatcc tcaaaaagtg                                               20

<210> SEQ ID NO 101
<211> LENGTH: 18
<212> TYPE: DNA
<213> ORGANISM: Artificial Sequence
<220> FEATURE:
<223> OTHER INFORMATION: Synthetic

<400> SEQUENCE: 101
caggacctgg ccgatgag                                                 18

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
```
agtttctgcc aaaacaccag 20

<210> SEQ ID NO 103
<211> LENGTH: 18
<212> TYPE: DNA
<213> ORGANISM: Artificial Sequence
<220> FEATURE:
<223> OTHER INFORMATION: Synthetic

<400> SEQUENCE: 103
tacacgaggc ccacaggt 18

<210> SEQ ID NO 104
<211> LENGTH: 25
<212> TYPE: DNA
<213> ORGANISM: Artificial Sequence
<220> FEATURE:
<223> OTHER INFORMATION: Synthetic

<400> SEQUENCE: 104
ttatttgaat ggaattttct taacc 25

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ccagaagtgc tgactgtgga 20

<210> SEQ ID NO 106
<211> LENGTH: 18
<212> TYPE: DNA
<213> ORGANISM: Artificial Sequence
<220> FEATURE:
<223> OTHER INFORMATION: Synthetic

<400> SEQUENCE: 106
aggtgatccg cctccttc 18

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
tgcacaggca gttttactgg 20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
tgatactgtt gcggtcttgc 20

<210> SEQ ID NO 109
<211> LENGTH: 20
<212> TYPE: DNA
<213> ORGANISM: Artificial Sequence
<220> FEATURE:

<223> OTHER INFORMATION: Synthetic

<400> SEQUENCE: 109
ccttgtgtcc acgctcctta                                          20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
aaggctcctc agccttttgt                                          20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
gtgtccccac gttttcattt                                          20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
aattacctgc gctcttttcg                                          20

<210> SEQ ID NO 113
<211> LENGTH: 24
<212> TYPE: DNA
<213> ORGANISM: Artificial Sequence
<220> FEATURE:
<223> OTHER INFORMATION: Synthetic

<400> SEQUENCE: 113
gagagttctt tatgctctcc ttgc                                     24

<210> SEQ ID NO 114
<211> LENGTH: 19
<212> TYPE: DNA
<213> ORGANISM: Artificial Sequence
<220> FEATURE:
<223> OTHER INFORMATION: Synthetic

<400> SEQUENCE: 114
gaggccaact ctcgtgctc                                           19

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gcactattcg gcttcctctg                                          20

<210> SEQ ID NO 116

```
<211> LENGTH: 20
<212> TYPE: DNA
<213> ORGANISM: Artificial Sequence
<220> FEATURE:
<223> OTHER INFORMATION: Synthetic

<400> SEQUENCE: 116
gcgattccta tccccattct                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
gaatctagca gccaggttgg                                              20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
atcttcctcc ccatgaatcc                                              20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
gagactggga tgtgcagagg                                              20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
gggggacaga taggtgtcaa                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
tgggtgtgat ctcacgtgtt                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
```
accaactgac cctgctccta                                          20

<210> SEQ ID NO 123
<211> LENGTH: 23
<212> TYPE: DNA
<213> ORGANISM: Artificial Sequence
<220> FEATURE:
<223> OTHER INFORMATION: Synthetic

<400> SEQUENCE: 123
ggtagacagg tgagaatgga gag                                      23

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
acagtgatgt gcaggtgagg                                          20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
acgttcaggg gctagtccag                                          20

<210> SEQ ID NO 126
<211> LENGTH: 18
<212> TYPE: DNA
<213> ORGANISM: Artificial Sequence
<220> FEATURE:
<223> OTHER INFORMATION: Synthetic

<400> SEQUENCE: 126
gaggctgggc actcgaag                                            18

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
tcttaaatgt tgccccatcc                                          20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
cagcgagcat ggtattgcta                                          20

<210> SEQ ID NO 129
<211> LENGTH: 18
<212> TYPE: DNA
<213> ORGANISM: Artificial Sequence
<220> FEATURE:

<223> OTHER INFORMATION: Synthetic

<400> SEQUENCE: 129
ctgggctccc agactcct                                                        18

<210> SEQ ID NO 130
<211> LENGTH: 22
<212> TYPE: DNA
<213> ORGANISM: Artificial Sequence
<220> FEATURE:
<223> OTHER INFORMATION: Synthetic

<400> SEQUENCE: 130
agttctgagg tcttttcaag ca                                                   22

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
tcctgttgag tggcagatgt                                                      20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
atcctttcct tggtgcctct                                                      20

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
aatgctttga atgatggcaa c                                                    21

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
tcgagactgt gccatagacg                                                      20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
ggaaaggagc cacatacagc                                                      20

<210> SEQ ID NO 136

```
<211> LENGTH: 20
<212> TYPE: DNA
<213> ORGANISM: Artificial Sequence
<220> FEATURE:
<223> OTHER INFORMATION: Synthetic

<400> SEQUENCE: 136
caggagcttg aacagcatca                                              20

<210> SEQ ID NO 137
<211> LENGTH: 18
<212> TYPE: DNA
<213> ORGANISM: Artificial Sequence
<220> FEATURE:
<223> OTHER INFORMATION: Synthetic

<400> SEQUENCE: 137
ctatgcccct ccgtcctc                                                18

<210> SEQ ID NO 138
<211> LENGTH: 28
<212> TYPE: DNA
<213> ORGANISM: Artificial Sequence
<220> FEATURE:
<223> OTHER INFORMATION: Synthetic

<400> SEQUENCE: 138
aatcacatac atgccttttt ccagttct                                     28

<210> SEQ ID NO 139
<211> LENGTH: 22
<212> TYPE: DNA
<213> ORGANISM: Artificial Sequence
<220> FEATURE:
<223> OTHER INFORMATION: Synthetic

<400> SEQUENCE: 139
ttcacctgga tctaacacga tg                                           22

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
tcagatgggc atactcctga                                              20

<210> SEQ ID NO 141
<211> LENGTH: 24
<212> TYPE: DNA
<213> ORGANISM: Artificial Sequence
<220> FEATURE:
<223> OTHER INFORMATION: Synthetic

<400> SEQUENCE: 141
tgtcatggtt ggattacttc ttca                                         24

<210> SEQ ID NO 142
<211> LENGTH: 23
<212> TYPE: DNA
<213> ORGANISM: Artificial Sequence
<220> FEATURE:
<223> OTHER INFORMATION: Synthetic

<400> SEQUENCE: 142
```

```
tcagttttac cagatccttt tgt                                          23

<210> SEQ ID NO 143
<211> LENGTH: 22
<212> TYPE: DNA
<213> ORGANISM: Artificial Sequence
<220> FEATURE:
<223> OTHER INFORMATION: Synthetic

<400> SEQUENCE: 143
cagcctggta ccatgtttta ct                                           22

<210> SEQ ID NO 144
<211> LENGTH: 23
<212> TYPE: DNA
<213> ORGANISM: Artificial Sequence
<220> FEATURE:
<223> OTHER INFORMATION: Synthetic

<400> SEQUENCE: 144
tgtacctaat ttggggtcaa aaa                                          23

<210> SEQ ID NO 145
<211> LENGTH: 25
<212> TYPE: DNA
<213> ORGANISM: Artificial Sequence
<220> FEATURE:
<223> OTHER INFORMATION: Synthetic

<400> SEQUENCE: 145
tccatgagat aaaagtcttc atttg                                        25

<210> SEQ ID NO 146
<211> LENGTH: 22
<212> TYPE: DNA
<213> ORGANISM: Artificial Sequence
<220> FEATURE:
<223> OTHER INFORMATION: Synthetic

<400> SEQUENCE: 146
tgttttgctt ctctttgtgc at                                           22

<210> SEQ ID NO 147
<211> LENGTH: 22
<212> TYPE: DNA
<213> ORGANISM: Artificial Sequence
<220> FEATURE:
<223> OTHER INFORMATION: Synthetic

<400> SEQUENCE: 147
ttttgtctcc ttcagcttcc tt                                           22

<210> SEQ ID NO 148
<211> LENGTH: 21
<212> TYPE: DNA
<213> ORGANISM: Artificial Sequence
<220> FEATURE:
<223> OTHER INFORMATION: Synthetic

<400> SEQUENCE: 148
gcatcacaac acaagcttca a                                            21

<210> SEQ ID NO 149
<211> LENGTH: 25
<212> TYPE: DNA
<213> ORGANISM: Artificial Sequence
<220> FEATURE:
```

<223> OTHER INFORMATION: Synthetic

<400> SEQUENCE: 149
gctgtttttc tttgagaatc ttttt                                              25

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
tggcagaaca gaatccctct                                                    20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
tgaggtgagc agagatcgtg                                                    20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
taccaaacca atggcagtga                                                    20

<210> SEQ ID NO 153
<211> LENGTH: 21
<212> TYPE: DNA
<213> ORGANISM: Artificial Sequence
<220> FEATURE:
<223> OTHER INFORMATION: Synthetic

<400> SEQUENCE: 153
tgctgtctct ttgaattttg g                                                  21

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
aggaagggaa ggcaatgaag                                                    20

<210> SEQ ID NO 155
<211> LENGTH: 21
<212> TYPE: DNA
<213> ORGANISM: Artificial Sequence
<220> FEATURE:
<223> OTHER INFORMATION: Synthetic

<400> SEQUENCE: 155
ccctttaccc ttctacctcc a                                                  21

<210> SEQ ID NO 156

```
<211> LENGTH: 20
<212> TYPE: DNA
<213> ORGANISM: Artificial Sequence
<220> FEATURE:
<223> OTHER INFORMATION: Synthetic

<400> SEQUENCE: 156
tatgcttccc aagctggtct                                              20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
tcaacgcagc aggatctaaa                                              20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
aggtttgcac caccacactt                                              20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
aggtgatcca gcctcctctg                                              20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
gaatgcaagg ctggtaaagg                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
caaggacgac atgcaaattc                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
```
gcgtcttttg gaaggagtga                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
tacagcccag aagggttacg                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
aatcagagat ggggctttt                                               20

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
tgcagaggtt gacttttcct g                                            21

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
tcacacttgg gctgtttcct                                              20

<210> SEQ ID NO 167
<211> LENGTH: 22
<212> TYPE: DNA
<213> ORGANISM: Artificial Sequence
<220> FEATURE:
<223> OTHER INFORMATION: Synthetic

<400> SEQUENCE: 167
tttgctccta atgaagagtt cg                                           22

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
cttcagggaa cctgtccaaa                                              20

<210> SEQ ID NO 169
<211> LENGTH: 21
<212> TYPE: DNA
<213> ORGANISM: Artificial Sequence
<220> FEATURE:

-continued

<223> OTHER INFORMATION: Synthetic

<400> SEQUENCE: 169
cgtgtttgag ttgtttgctt g                                     21

<210> SEQ ID NO 170
<211> LENGTH: 18
<212> TYPE: DNA
<213> ORGANISM: Artificial Sequence
<220> FEATURE:
<223> OTHER INFORMATION: Synthetic

<400> SEQUENCE: 170
gctcagctgc ctcagcat                                         18

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tgggtatctc agaggccaga                                       20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
aacaggacat ccgcttatgg                                       20

<210> SEQ ID NO 173
<211> LENGTH: 23
<212> TYPE: DNA
<213> ORGANISM: Artificial Sequence
<220> FEATURE:
<223> OTHER INFORMATION: Synthetic

<400> SEQUENCE: 173
ttggtgtttt tcttacctcc aga                                   23

<210> SEQ ID NO 174
<211> LENGTH: 21
<212> TYPE: DNA
<213> ORGANISM: Artificial Sequence
<220> FEATURE:
<223> OTHER INFORMATION: Synthetic

<400> SEQUENCE: 174
ccgtagtgga ctcaacatcc a                                     21

<210> SEQ ID NO 175
<211> LENGTH: 25
<212> TYPE: DNA
<213> ORGANISM: Artificial Sequence
<220> FEATURE:
<223> OTHER INFORMATION: Synthetic

<400> SEQUENCE: 175
aaaatttata tgagattgtt tgctg                                 25

<210> SEQ ID NO 176

```
<211> LENGTH: 20
<212> TYPE: DNA
<213> ORGANISM: Artificial Sequence
<220> FEATURE:
<223> OTHER INFORMATION: Synthetic

<400> SEQUENCE: 176
actcaaccac cagctccaac                                                  20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
tcattccccc agagaatcat                                                  20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
agcttgggca acaagaacaa                                                  20

<210> SEQ ID NO 179
<211> LENGTH: 21
<212> TYPE: DNA
<213> ORGANISM: Artificial Sequence
<220> FEATURE:
<223> OTHER INFORMATION: Synthetic

<400> SEQUENCE: 179
ttgcaagaca atgtttttgt g                                                21

<210> SEQ ID NO 180
<211> LENGTH: 21
<212> TYPE: DNA
<213> ORGANISM: Artificial Sequence
<220> FEATURE:
<223> OTHER INFORMATION: Synthetic

<400> SEQUENCE: 180
ttgctgcctg aatattgtga a                                                21

<210> SEQ ID NO 181
<211> LENGTH: 22
<212> TYPE: DNA
<213> ORGANISM: Artificial Sequence
<220> FEATURE:
<223> OTHER INFORMATION: Synthetic

<400> SEQUENCE: 181
tggaagagga atgatggaga tt                                               22

<210> SEQ ID NO 182
<211> LENGTH: 21
<212> TYPE: DNA
<213> ORGANISM: Artificial Sequence
<220> FEATURE:
<223> OTHER INFORMATION: Synthetic

<400> SEQUENCE: 182
```
ggagcctctt agcaatcact c                                              21

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
gctcatggac ctgtcatcct                                                20

<210> SEQ ID NO 184
<211> LENGTH: 21
<212> TYPE: DNA
<213> ORGANISM: Artificial Sequence
<220> FEATURE:
<223> OTHER INFORMATION: Synthetic

<400> SEQUENCE: 184
cagtgccatc agcactactc a                                              21

<210> SEQ ID NO 185
<211> LENGTH: 21
<212> TYPE: DNA
<213> ORGANISM: Artificial Sequence
<220> FEATURE:
<223> OTHER INFORMATION: Synthetic

<400> SEQUENCE: 185
gacttcagcc cctaagaatg c                                              21

<210> SEQ ID NO 186
<211> LENGTH: 21
<212> TYPE: DNA
<213> ORGANISM: Artificial Sequence
<220> FEATURE:
<223> OTHER INFORMATION: Synthetic

<400> SEQUENCE: 186
aggctgagac agaactgctt g                                              21

<210> SEQ ID NO 187
<211> LENGTH: 19
<212> TYPE: DNA
<213> ORGANISM: Artificial Sequence
<220> FEATURE:
<223> OTHER INFORMATION: Synthetic

<400> SEQUENCE: 187
gaccctcagg ccatcattt                                                 19

<210> SEQ ID NO 188
<211> LENGTH: 22
<212> TYPE: DNA
<213> ORGANISM: Artificial Sequence
<220> FEATURE:
<223> OTHER INFORMATION: Synthetic

<400> SEQUENCE: 188
tcagcacaga acctgataca ca                                             22

<210> SEQ ID NO 189
<211> LENGTH: 19
<212> TYPE: DNA
<213> ORGANISM: Artificial Sequence
<220> FEATURE:

<223> OTHER INFORMATION: Synthetic

<400> SEQUENCE: 189
tcaccgatct cctcctcct                                           19

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
tgcccagaga atcctcctta                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
ttgctgcgaa acaaacattc                                          20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
gagacaccgt ttgggaagat                                          20

<210> SEQ ID NO 193
<211> LENGTH: 19
<212> TYPE: DNA
<213> ORGANISM: Artificial Sequence
<220> FEATURE:
<223> OTHER INFORMATION: Synthetic

<400> SEQUENCE: 193
ccatagttca cggggttgg                                           19

<210> SEQ ID NO 194
<211> LENGTH: 19
<212> TYPE: DNA
<213> ORGANISM: Artificial Sequence
<220> FEATURE:
<223> OTHER INFORMATION: Synthetic

<400> SEQUENCE: 194
cccgaggtcg tcttcattt                                           19

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
gcaacggagg caaactagac                                          20

<210> SEQ ID NO 196

-continued

```
<211> LENGTH: 18
<212> TYPE: DNA
<213> ORGANISM: Artificial Sequence
<220> FEATURE:
<223> OTHER INFORMATION: Synthetic

<400> SEQUENCE: 196
gagagcgggt cagggttt                                                 18

<210> SEQ ID NO 197
<211> LENGTH: 18
<212> TYPE: DNA
<213> ORGANISM: Artificial Sequence
<220> FEATURE:
<223> OTHER INFORMATION: Synthetic

<400> SEQUENCE: 197
aggccctcaa accctgac                                                 18

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
tcctccacca ccttcatctt                                               20

<210> SEQ ID NO 199
<211> LENGTH: 18
<212> TYPE: DNA
<213> ORGANISM: Artificial Sequence
<220> FEATURE:
<223> OTHER INFORMATION: Synthetic

<400> SEQUENCE: 199
gttgctcctc gggctctc                                                 18

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
aaggctgaca aaccaatgct                                               20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
aagatgaagg tggtggagga                                               20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
```
acctctcgga aaggaaagga            20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
cagactctgc cagtctttgc            20

<210> SEQ ID NO 204
<211> LENGTH: 18
<212> TYPE: DNA
<213> ORGANISM: Artificial Sequence
<220> FEATURE:
<223> OTHER INFORMATION: Synthetic

<400> SEQUENCE: 204
ctcccactcg tgccagat              18

<210> SEQ ID NO 205
<211> LENGTH: 18
<212> TYPE: DNA
<213> ORGANISM: Artificial Sequence
<220> FEATURE:
<223> OTHER INFORMATION: Synthetic

<400> SEQUENCE: 205
agggatccca aagcagca              18

<210> SEQ ID NO 206
<211> LENGTH: 18
<212> TYPE: DNA
<213> ORGANISM: Artificial Sequence
<220> FEATURE:
<223> OTHER INFORMATION: Synthetic

<400> SEQUENCE: 206
accccactgg gctcaact              18

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
agctgagcct ggcttctctt            20

<210> SEQ ID NO 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
gccagcatcc tcaaaaagtg            20

<210> SEQ ID NO 209
<211> LENGTH: 18
<212> TYPE: DNA
<213> ORGANISM: Artificial Sequence
<220> FEATURE:

<223> OTHER INFORMATION: Synthetic

<400> SEQUENCE: 209
caggacctgg ccgatgag                                              18

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
agtttctgcc aaaacaccag                                            20

<210> SEQ ID NO 211
<211> LENGTH: 18
<212> TYPE: DNA
<213> ORGANISM: Artificial Sequence
<220> FEATURE:
<223> OTHER INFORMATION: Synthetic

<400> SEQUENCE: 211
tacacgaggc ccacaggt                                              18

<210> SEQ ID NO 212
<211> LENGTH: 25
<212> TYPE: DNA
<213> ORGANISM: Artificial Sequence
<220> FEATURE:
<223> OTHER INFORMATION: Synthetic

<400> SEQUENCE: 212
ttatttgaat ggaattttct taacc                                      25

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
ccagaagtgc tgactgtgga                                            20

<210> SEQ ID NO 214
<211> LENGTH: 18
<212> TYPE: DNA
<213> ORGANISM: Artificial Sequence
<220> FEATURE:
<223> OTHER INFORMATION: Synthetic

<400> SEQUENCE: 214
aggtgatccg cctccttc                                              18

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
tgcacaggca gttttactgg                                            20

<210> SEQ ID NO 216

```
<211> LENGTH: 20
<212> TYPE: DNA
<213> ORGANISM: Artificial Sequence
<220> FEATURE:
<223> OTHER INFORMATION: Synthetic

<400> SEQUENCE: 216
tgatactgtt gcggtcttgc                                               20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
ccttgtgtcc acgctcctta                                               20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
aaggctcctc agccttttgt                                               20

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
gtgtccccac gttttcattt                                               20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
aattacctgc gctcttttcg                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
gctctccttg caacttcctg                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
```

```
gggcagtagc aagtcgtcgt                                                20

<210> SEQ ID NO 223
<211> LENGTH: 19
<212> TYPE: DNA
<213> ORGANISM: Artificial Sequence
<220> FEATURE:
<223> OTHER INFORMATION: Synthetic

<400> SEQUENCE: 223
tcctctggga agcgtccgg                                                 19

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
gttaagtgac ttgaacacgg                                                20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
aggttgggat ggctagggag                                                20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
ctccctagcc atcccaacct                                                20

<210> SEQ ID NO 227
<211> LENGTH: 19
<212> TYPE: DNA
<213> ORGANISM: Artificial Sequence
<220> FEATURE:
<223> OTHER INFORMATION: Synthetic

<400> SEQUENCE: 227
ggagacgagc aaggaggct                                                 19

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
ccagaaagca ggtagagtca                                                20

<210> SEQ ID NO 229
<211> LENGTH: 20
<212> TYPE: DNA
<213> ORGANISM: Artificial Sequence
<220> FEATURE:
```

```
<223> OTHER INFORMATION: Synthetic

<400> SEQUENCE: 229
gctctgcact gtggaaggaa                                                 20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
agggactgca gcaatttctg                                                 20

<210> SEQ ID NO 231
<211> LENGTH: 19
<212> TYPE: DNA
<213> ORGANISM: Artificial Sequence
<220> FEATURE:
<223> OTHER INFORMATION: Synthetic

<400> SEQUENCE: 231
gggcagcctg gagggagtt                                                  19

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
gagacagaag cagcagagga                                                 20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
caggtatcct gtcctgtcga                                                 20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
ggagagctgg tcccgcttcc                                                 20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
actgcagcaa acctgtcctt                                                 20

<210> SEQ ID NO 236
```

```
-continued
<211> LENGTH: 20
<212> TYPE: DNA
<213> ORGANISM: Artificial Sequence
<220> FEATURE:
<223> OTHER INFORMATION: Synthetic

<400> SEQUENCE: 236
ggaggaggga gactctttgg                                              20
```